US012807727B2

(12) United States Patent
Yuan et al.

(10) Patent No.: US 12,807,727 B2
(45) Date of Patent: Nov. 24, 2026

(54) BISPECIFIC ANTIBODY BINDING TO BCMA AND CD3, AND PREPARATION METHOD THEREFOR AND USE THEREOF

(71) Applicant: EXCYTE BIOPHARMA LTD, Beijing (CN)

(72) Inventors: Andy Yuan, Beijing (CN); Lili Bai, Beijing (CN); Qingwu Meng, Beijing (CN); Likun Zhao, Beijing (CN); Yijia Li, Beijing (CN); Yanhu Li, Beijing (CN)

(73) Assignee: EXCYTE BIOPHARMA LTD, Beijing (CN)

(*) Notice: Subject to any disclaimer, the term of this patent is extended or adjusted under 35 U.S.C. 154(b) by 278 days.

(21) Appl. No.: 18/256,316

(22) PCT Filed: May 5, 2022

(86) PCT No.: PCT/CN2022/090931
§ 371 (c)(1),
(2) Date: Jun. 7, 2023

(87) PCT Pub. No.: WO2022/267702
PCT Pub. Date: Dec. 29, 2022

(65) Prior Publication Data

US 2025/0011447 A1 Jan. 9, 2025

(30) Foreign Application Priority Data

Jun. 24, 2021 (CN) ........................ 202110704255.6

(51) Int. Cl.
*C07K 16/28* (2006.01)

(52) U.S. Cl.
CPC ...... *C07K 16/2878* (2013.01); *C07K 16/2809* (2013.01); *C07K 2317/31* (2013.01); *C07K 2317/52* (2013.01); *C07K 2317/565* (2013.01); *C07K 2317/73* (2013.01); *C07K 2317/92* (2013.01)

(58) Field of Classification Search
None
See application file for complete search history.

(56) References Cited

U.S. PATENT DOCUMENTS

2013/0273055 A1* 10/2013 Borges .................... A61P 37/02 530/387.3

FOREIGN PATENT DOCUMENTS

| | | | | |
|---|---|---|---|---|
| CN | 109776683 A | * 5/2019 | | C07K 16/468 |
| CN | 109843325 A | 6/2019 | | |
| CN | 110431151 A | 11/2019 | | |
| CN | 112368019 A | 2/2021 | | |
| CN | 112574308 A | 3/2021 | | |
| CN | 113061185 A | 7/2021 | | |
| EP | 3029068 A1 | 6/2016 | | |
| JP | 2018525005 A | 9/2018 | | |
| JP | 2019147793 A | 9/2019 | | |
| WO | WO 2002/066516 A2 | 8/2002 | | |
| WO | 2013072415 A1 | 5/2013 | | |
| WO | 2016020332 A1 | 2/2016 | | |
| WO | 2018083204 A1 | 5/2018 | | |
| WO | 2018119215 A1 | 6/2018 | | |
| WO | 2019220368 A1 | 11/2019 | | |
| WO | 2020191346 A1 | 9/2020 | | |
| WO | WO 2020/186974 A1 | 9/2020 | | |
| WO | 2020261093 A1 | 12/2020 | | |
| WO | WO 2021/063349 A1 | 4/2021 | | |
| WO | 2021092056 A1 | 5/2021 | | |

OTHER PUBLICATIONS

Janeway et al., Immunobiology, 3rd edition, Garland Publishing Inc., 1997, pp. 3:1-3:11.*
Rudikoff et al., Proc Natl Acad Sci U S A. Mar. 1982;79(6):1979-83. doi: 10.1073/pnas.79.6.1979. PMID: 6804947.*
Edwards et al., J Mol Biol. Nov. 14, 2003;334(1):103-18. doi: 10.1016/j.jmb.2003.09.054. PMID: 14596803.*
Llyod et al., Protein Eng Des Sel. Mar. 2009;22(3):159-68. doi: 10.1093/protein/gzn058. Epub Oct. 29, 2008. PMID: 18974080.*
Goel et al., J Immunol. Dec. 15, 2004; 173(12):7358-67 PMID: 15585860 DOI: 10.4049/jimmunol.173. 12.7358.*
Lescar et al., J Biol Chem. Jul. 28, 1995;270(30):18067-76. doi: 10.1074/jbc.270.30.18067. PMID: 7629116.*
Kanyavuz et al., Nat Rev Immunol. Jun. 2019; 19(6):355-368. doi: 10.1038/S41577-019-0126-7. PMID: 30718829.*
Winkler et al., J Immunol. Oct. 15, 2000, 165(8):4505-14. doi: 10.4049/jimmunol.165.8.4505. PMID: 11035090.*
Caraccio et al., "Bispecific Antibodies for Multiple Myeloma: A Review of Targets, Drugs, Clinical Trials, and Future Directions", Frontiers in Immunology, 2020, in 2 pages.
Dilillo et al., "REGN5458, a Bispecific BCMAxCD3 T Cell Engaging Antibody, Demonstrates Robust In Vitro and In Vivo Anti-Tumor Efficacy in Multiple Myeloma Models, Comparable to That of BCMA CAR T Cells", Blood Advances, 2018, vol. 132, Issue Supplement 1, in 7 pages.
International Search Report issued in International Application No. PCT/CN2022/090931, mailed on Jul. 27, 2022.

(Continued)

*Primary Examiner* — Michael Szperka
(74) *Attorney, Agent, or Firm* — NK Patent Law

(57) ABSTRACT

A bispecific antibody binding to BCMA and CD3, and a preparation method therefor and the use thereof. A bispecific antibody, which can bind to BCMA and CD3 simultaneously, has specific targeting effects and can efficiently stimulate directed immune responses. The bispecific antibody retains the biological functions of an anti-CD3 antibody and an anti-BCMA antibody, enables the bispecific antibody molecule to achieve excellent biological functions of simultaneously binding to BCMA and CD3 in a targeted manner, forms a bridge between tumor cells and immune effector cells, effectively activates the immune effector cells and the directed immune responses, significantly enhances the effects of immune cells in killing tumor cells, has a high targeted cell killing efficiency, reduces the ADCC effect to the largest extent, has high safety, and has good application prospects in tumor immunotherapy.

10 Claims, 8 Drawing Sheets

Specification includes a Sequence Listing.

(56) References Cited

OTHER PUBLICATIONS

Anonymous: "CD3/BCMA Bispecific Antibody for Multiple Myeloma Treatment", Protheragen, Jan. 26, 2021 (Jan. 26, 2021), XP093181789, Retrieved from the Internet: URL:https://web.archive.org/web/20210126090624/https://www.protheragen.com/available-projects/cd3-bcma-bispecific-antibody-for-multiple-myeloma-treatment/.
CIPO, Office Action for corresponding Canadian Patent Application No. 3,222,339, May 30, 2025, 4 pages.
Dililo et al.: "A BCMAxCD3 bispecific T cell-engaging antibody demonstrates robust antitumor efficacy similar to that of anti-BCMA CART cells", Regeneron Pharmaceuticals, Tarrytown, NY, Mar. 9, 2021, vol. 5, No. 5, pp. 1291-1304.
EPO, Extended European Search Report for corresponding European Patent Application No. 22827200.1, Jul. 26, 2024, 16 pages.
IP Australia, Office Action for corresponding Australian Patent Application No. 2022298402, Sep. 17, 2025, 5 pages.

* cited by examiner

| No. of peak | Retention time (min) | Peak area (mAU*S) | % Area | Peak height (mAU) |
|---|---|---|---|---|
| 1 | 10.577 | 12275.2 | 100 | 421.905 |

| No. of peak | Retention time (min) | Peak area (mAU*S) | % Area | Peak height (mAU) |
|---|---|---|---|---|
| 2 | 10.537 | 12102.3 | 99.96 | 411.7719 |

A

B

| | B10.9K3 | B10.5K3 | B10.4K3 | B10.3K3 | B10K3 | B10(high)K3 |
|---|---|---|---|---|---|---|
| EC50，pM | 8.759 | 12.87 | 7.839 | 5.833 | N/A | 281.7 |

A

B

BISPECIFIC ANTIBODY BINDING TO BCMA AND CD3, AND PREPARATION METHOD THEREFOR AND USE THEREOF

CROSS-REFERENCE TO RELATED APPLICATION

The present application claims priority to Chinese Patent Application No. 202110704255.6, entitled "Bispecific antibody binding to BCMA and CD3, and preparation method therefor and use thereof", and filed on Jun. 24, 2021, the entire disclosure of which is incorporated herein by reference in its entirety.

TECHNICAL FIELD

The disclosure provided herein relates to the technical field of genetic engineering antibody, and in particular to a bispecific antibody binding to BCMA and CD3 and preparation method therefor and use thereof.

BACKGROUND ART

Monoclonal antibodies can be used clinically for treatment of tumors, immune disease and infection, which are most widely used in tumor therapy. The Monoclonal antibody therapy against tumor is a kind of immunotherapy directed against specific targets of diseased cells to stimulate the immune system to kill target cells. To further improve drug efficacy and reduce side effects, new monoclonal antibodies-based medicines, including antibody drug conjugate (ADC), bispecific antibody (bsAb), chimeric antigen receptor T cells (CAR-T) and other new protein and cell-based drugs are developing rapidly. The cell-bridging bispecific antibody based on bispecificity has significantly improved cell killing activity and specificity due to its ability of connecting immune T cells and targeted cancer cells, which has groundbreaking clinical value, thereby attracting extra attention. For multiple myeloma, the cell-bridging bispecific antibody targeting BCMA with the above properties is one of the development directions to improve the effect of the antibody therapy and has become a hot spot in the field of antibody engineering research.

The CD3 molecule on the surface of T cells is composed of four subunits: δ, ε, γ, and ζ, with the molecular weight of 18.9 kDa, 23.1 kDa, 20.5 kDa, and 18.7 kDa, with the length of 171, 207, 182, and 164 amino acid residues, respectively. Together, they form 6 peptide chains, and form one active intact TCR complex, whose structural diagram is shown in graph A of FIG. 1. The complex has the functions of T cell activation, signal transduction and stabilization TCR structure. The cytoplasmic segment of CD3 contains immunoreceptor tyrosine-based activation motif (ITAM), and TCR recognizes and binds to the antigen peptide presented by major histo-compatibility complex (MHC) molecules, resulting in phosphorylation of the tyrosine residue in the conservative sequence of ITAM ITAM by the tyrosine protein kinase p56lck in T cells, and other tyrosine protein kinases containing Scr homology 2 (SH2) domain (such as ZAP-70) are then recruited. The phosphorylation of ITAM and its binding to ZAP-70 is one of the important biochemical reactions in the early stage of signal transduction of T cell activation. Therefore, the function of the CD3 molecule is to transduce the activation signal generated by the antigen recognition by TCR.

BCMA (B-cell maturation antigen, TNFRSF17, CD269) is a non-glycosylated type I transmembrane protein, which a member of the tumor necrosis (TNF) receptor superfamily that is preferentially expressed in differentiated plasma cells, involved in maturation, growth and survival of B cells. BCMA is originally reported as a Golgi integral membrane protein of human mature B lymphocytes, i.e., as an intracellular protein, suggesting that BCMA appears to have an important role in B-cell development and homeostasis.

BCMA expression is restricted to the B-cell lineage, which is predominantly expressed on plasma cells and plasma blasts (Graph B, FIG. 1), and to some extent on memory B-cells, but not on peripheral B-cells. BCMA is also expressed on multiple myeloma (MM) cells. BCMA regulates different aspects of humoral immunity, B-cell development and homeostasis, with its family members transmembrane activator and cyclophilin ligand interactor (TACI) and the B-cell activating factor of the TNF family receptor (BAFF-R). BCMA is the receptor for two ligands of the TNF superfamily (graph C, FIG. 1): APRIL (a proliferation-inducing ligand, CD256, TNFSF13), binding to BCMA with high affinity, and B-cell activating factor BAFF (THANK, BlyS, B lymphocyte stimulator, TALL-1 and zTNF4), binding to BCMA with low affinity. APRIL and BAFF show structural similarities as well as overlapping but distinct receptor-binding specificities. The negative regulator TACI also binds to both BAFF and APRIL. Cooperative binding of APRIL and BAFF to BCMA and/or TACI activates the transcription factor NF-κB, increases the expression of prosurvival Bcl-2 family members (e.g., Bcl-2, Bcl-xL, Bcl-w, Mcl-1, A1), and down-regulates the expression of pro-apoptotic factors (e.g., Bid, Bad, Bik, Bim, etc.), thereby inhibiting apoptosis and promoting survival, which promotes B cell differentiation, proliferation, survival and antibody production. The expression of BCMA occurs at later stages of B-cell differentiation and is conducive to the long-term survival of plasma blasts and plasma cells in bone marrow.

BCMA is an extremely important B-cell biomarker that is widely expressed on the surface of MM cells, which is a popular immunotherapy target for MM and other hematological malignancies. BCMA has always been the focus of three consecutive ASCO annual conferences. BCMA has become the second most popular target for anticancer therapy after CD19, according to a new analysis by the National Cancer Institute (CRI). MM is heterogeneous and is mostly caused by chromosomal translocation of t(11:14), t(4:14), t(8:14), del(13), del(17) (among others). Patients with MM may experience a variety of disease-related symptoms due to bone marrow infiltration, bone destruction, renal failure, immunodeficiency, and the psychological burden of a cancer diagnosis.

MM remains difficult to treat, since side effects always occur during treatment such as chemotherapy and stem cell transplantation, despite their efficacy in improving survival. Almost all patients may eventually experience relapse, despite significant advances in chemotherapy, proteasome inhibitors, immunomodulators thalidomide derivatives, and CD38-targeting antibodies. Therefore, there is still an urgent need for new medicines in this field. To date, the two most used treatment options for multiple myeloma patients include a combination of steroids, thalidomide, lenalidomide, bortezomib, or a variety of cytotoxic agents, as well as high-dose chemotherapy combined with autologous stem cell transplantation for younger patients. Most procedures are autologous transplantations, which use the patient's own cells. Although the transplantation is not curative, it has been shown to prolong the survival of selected patients, which can be given as the initial therapy in newly diagnosed patients or at the time of relapse. Sometimes, more than one kind of transplants may be recommended for selected patients for adequate disease control. The combination of chemotherapy agents including cyclophosphamide, doxorubicin, vincristine, and melphalan, and immunomodulators such as thalidomide, lenalidomide, bortezomib, and corticosteroids (e.g., dexamethasone) has become an important option for the treatment of myeloma in newly diagnosed patients and those with advanced disease for who experience treatment failure with chemotherapy or transplantation.

The current therapies for MM are generally non-curative. The stem cell transplantation may not be an option for most patients, because of advanced age, the presence of other serious medical conditions, or other physical limitations. Chemotherapy can only achieve partial control of multiple myeloma, rarely reaching complete remission. Therefore, there is an urgent need for new innovative therapies.

The antagonistic BCMA-specific antibodies prevent NF-κB activation associated with a potent prosurvival signal-transduction pathway in normal and malignant B-cells.

Other therapies against hematogenous neoplasms or autoimmune disorders focus on the interaction between BAFF, APRIL (i.e., ligands of the TNF ligand superfamily) and receptors TACI, BAFF-R, and BCMA activated by BAFF and/or APRIL. For example, atacicept (TACI-Ig) is created by combining the Fc-domain of human immunoglobulin to Zymogenetics' TACI to neutralize both ligands and prevent receptor activation. Atacicept is currently in clinical trials for the treatment of systemic lupus erythematosus (SLE, phase III), multiple sclerosis (MS, phase II) and rheumatoid arthritis (RA, phase II), as well as malignant B-cell chronic lymphocytic leukemia (CLL), non-Hodgkin's lymphoma (NHL) and MM in phase I clinical trials. In preclinical studies, atacicept reduced the growth and survival of primary MM cells and MM cell lines in vitro and in vivo, suggesting the relevance of TACI ligands to MM cells. Given that most MM cells and their derived cell lines express both BCMA and TACI, their receptors may favor ligand-mediated growth and survival. These data suggest that antagonistic effect against BCMA and TACI may be conducive to the treatment of plasma cell disorders. In addition, BCMA-specific antibodies that cross-react with TACI have been described (WO02/066516).

Human Genome Sciences and GlaxoSmithKline have developed an antibody called belimumab that targets BAFF. Belimumab blocks the binding of soluble BAFF to its receptors BAFF-R, BCMA, and TACI on B cells. Belimumab does not directly bind B cells, but inhibits the survival of B cells, including autoreactive B cells, and reduces the differentiation of B cells into immunoglobulin-producing plasma cells through binding to BAFF.

Even though BCMA, BAFF-R and TACI (i.e., B cell receptors of the TNF receptor superfamily) and their ligands BAFF and APRIL are subject to treatment options against cancer and/or autoimmune disorders, there remains a need for other available options for the treatment of this medical condition.

SUMMARY OF THE INVENTION

The first objective of the present disclosure is to provide a bispecific antibody binding to BCMA and CD3 and its active fragments.

The second objective of the present disclosure is to provide nucleic acids encoding the above-mentioned antibody or its active fragments.

The third objective of the present disclosure is to provide the use of the aforementioned antibody or its active fragments.

Specifically, the present disclosure provides the following technical solutions:

Firstly, the present disclosure provides a bispecific antibody binding to BCMA and CD3, consisting of:

the first domain, binding to B cell maturation antigen BCMA, and the second domain, binding to T cell surface antigen CD3, wherein, the first domain and the second domain are connected by linker peptides, the first domain comprises the heavy chain variable region and the light chain variable region, and CDR1, CDR2, and CDR3 in the heavy chain variable regions have amino acid sequences represented by SEQ ID NOs.4-6 respectively or have amino acid sequences containing one or more of the following mutations when taking the amino acid sequences represented by SEQ ID NOs.4-6 as reference sequences:

(1) S at position 1 of the amino acid sequence represented by SEQ ID NO.4 is mutated to P or K;

(2) Y at position 2 of the amino acid sequence represented by SEQ ID NO.4 is mutated to H, D, G, M or S;

(3) A at position 3 of the amino acid sequence represented by SEQ ID NO.4 is mutated to N;

(4) S at position 5 of the amino acid sequence represented by SEQ ID NO.4 is mutated to H, N, A or M;

(5) G at position 1 of the amino acid sequence represented by SEQ ID NO.5 is mutated to V or T;

(6) I at position 3 of the amino acid sequence represented by SEQ ID NO.5 is mutated to H;

(7) I at position 4 of the amino acid sequence represented by SEQ ID NO.5 is mutated to D or A;

(8) F at position 5 of the amino acid sequence represented by SEQ ID NO.5 is mutated to H;

(9) T at position 7 of the amino acid sequence represented by SEQ ID NO.5 is mutated to K;

(10) F at position 4 of the amino acid sequence represented by SEQ ID NO.6 is mutated to L;

CDR1, CDR2 and CDR3 in the light chain variable regions of the first domain have amino acid sequences represented by SEQ ID NOs.1-3 respectively or have amino acid sequences containing one or more of the following mutations when taking the amino acid sequences represented by SEQ ID NOs.1-3 as reference sequences:

(1) S at position 5 of the amino acid sequence represented by SEQ ID NO.1 is mutated to N, R or T;

(2) L at position 7 of the amino acid sequence represented by SEQ ID NO.3 is mutated to Q, V or A;

(3) I at position 8 of the amino acid sequence represented by SEQ ID NO.3 is mutated to S, A, R or P;

(4) Y at position 10 of the amino acid sequence represented by SEQ ID NO.3 is mutated to M, L, W or T;

(5) V at position 11 of the amino acid sequence represented by SEQ ID NO.3 is mutated to L or Q.

The present disclosure screens the genetically engineered single-chain antibody against BCMA from a fully synthetic single-chain human antibody library, obtains the variable region gene sequences of the antibody, constructs the mutation library through a point mutation kit, to obtain clones with high affinity. The DNA of these clones is mixed, and the combinatorial library of single-chain antibody is assembled through recombination, and the BCMA antibodies with high affinity to human BCMA is obtained after screening.

The amino acid sequence pattern of the antibody variable region provided by the present disclosure is FR1-CDR1-FR2-CDR2-FR3-CDR3-FR4. In the present application, the division of regions of FR and CDR is based on Kabat Numbering. FR1 to FR4 herein represent four framework regions, and CDR1 to CDR3 indicate three hypervariable regions. FR1 to FR4 can be isolated from the constant region sequence (such as the most used amino acids of human immunoglobulin light and heavy chain class, subclass or subfamily), or isolated from a separate human antibody framework region or from combination of different framework region genes.

After further screening, the present disclosure provides the following bispecific antibodies, with the first domain having higher affinity to BCMA:

bispecific antibodies binding to BCMA and CD3, consisting of:

the first domain, binding to B-cell maturation antigen BCMA, and the second domain, binding to T cell surface antigen CD3, wherein the first domain and the second domain are connected by linker peptides, the first domain comprises the heavy chain variable region and the light chain variable region. In the heavy chain variable region, CDR1 has the amino acid sequence represented by any one of SEQ ID NOs.4, 7, 8 and 9, CDR2 has the amino acid sequence represented by any one of SEQ ID NOs.5 and 10, and CDR3 has the amino acid sequence represented by any one of SEQ ID NOs.6 and 11;

In the light chain variable region, CDR1 has the amino acid sequence represented by any one of SEQ ID NOs.1 and 12, CDR2 has the amino acid sequence represented by SEQ ID NO.2, and CDR3 has the amino acid sequence represented by any one of SEQ ID NO.3, 13, 14, 15 and 16.

Furthermore, among the above-mentioned antibodies that bind to BCMA, the following antibodies exhibit higher affinity to BCMA:

CDR region sequences in the heavy chain variable region are any of the following:

(1) CDR1 has the amino acid sequence represented by SEQ ID NO.4, CDR2 has the amino acid sequence represented by SEQ ID NO.5, and CDR3 has the amino acid sequence represented by SEQ ID NO.6;

(2) CDR1 has the amino acid sequence represented by SEQ ID NO.7, CDR2 has the amino acid sequence represented by SEQ ID NO.10, and CDR3 has the amino acid sequence represented by SEQ ID NO.11;

(3) CDR1 has the amino acid sequence represented by SEQ ID NO.8, CDR2 has the amino acid sequence represented by SEQ ID NO.10, the CDR3 has the amino acid sequence represented by SEQ ID NO.11;

(4) CDR1 has the amino acid sequence represented by SEQ ID NO.9, CDR2 has the amino acid sequence represented by SEQ ID NO.10, and CDR3 has the amino acid sequence represented by SEQ ID NO.11:

The CDR region sequences in the light chain variable region is any of the following:

(1) CDR1 has the amino acid sequence represented by SEQ ID NO.1, CDR2 has the amino acid sequence represented by SEQ ID NO.2, and CDR3 has the amino acid sequence represented by SEQ ID NO.3;

(2) CDR1 has the amino acid sequence represented by SEQ ID NO.12, CDR2 has the amino acid sequence represented by SEQ ID NO.2, and CDR3 has the amino acid sequence represented by SEQ ID NO.13;

(3) CDR1 has the amino acid sequence represented by SEQ ID NO.12, CDR2 has the amino acid sequence represented by SEQ ID NO.2, and CDR3 has the amino acid sequence represented by SEQ ID NO.14;

(4) CDR1 has the amino acid sequence represented by SEQ ID NO.12, CDR2 has the amino acid sequence represented by SEQ ID NO.2, and CDR3 has the amino acid sequence represented by SEQ ID NO.15;

(5) CDR1 has the amino acid sequence represented by SEQ ID NO.12, CDR2 has the amino acid sequence represented by SEQ ID NO.2, and CDR3 has the amino acid sequence represented by SEQ ID NO.16;

Furthermore, among the above-mentioned antibodies binding to BCMA, the following antibodies exhibit higher affinity to BCMA:

CDRs in the heavy chain variable region and CDRs in the light chain variable region is any of the following:

(1) In the heavy chain variable region, CDR1 has the amino acid sequence represented by SEQ ID NO.4, CDR2 has the amino acid sequence represented by SEQ ID NO.5, and CDR3 has the amino acid sequence represented by SEQ ID NO.6; In the light chain variable region, CDR1 has the amino acid sequence represented by SEQ ID NO.1, CDR2 has the amino acid sequence represented by SEQ ID NO.2, and CDR3 has the amino acid sequence represented by SEQ ID NO.3;

(2) In the heavy chain variable region, CDR1 has the amino acid sequence represented by SEQ ID NO.8, CDR2 has the amino acid sequence represented by SEQ ID NO.10, and CDR3 has the amino acid sequence represented by SEQ ID NO.11; In the light chain variable region, CDR1 has the amino acid sequence represented by SEQ ID NO.12, CDR2 has the amino acid sequence represented by SEQ ID NO.2, and CDR3 has the amino acid sequence represented by SEQ ID NO.13;

(3) In the heavy chain variable region, CDR1 has the amino acid sequence represented by SEQ ID NO.9, CDR2 has the amino acid sequence represented by SEQ ID NO.10, and CDR3 has the amino acid sequence represented by SEQ ID NO.11; In the light chain variable region, CDR1 has the amino acid sequence represented by SEQ ID NO.1, CDR2 has the amino acid sequence represented by SEQ ID NO.2, and CDR3 has the amino acid sequence represented by SEQ ID NO.3;

(4) In the heavy chain variable region, CDR1 has the amino acid sequence represented by SEQ ID NO.8, CDR2 has the amino acid sequence represented by SEQ ID NO.10, and CDR3 has the amino acid sequence represented by SEQ ID NO.11; In the light chain variable region, CDR1 has the amino acid sequence represented by SEQ ID NO.12, CDR2 has the amino acid sequence represented by SEQ ID NO.2, and CDR3 has the amino acid sequence represented by SEQ ID NO.16.

Based on the sequences of the above-mentioned CDRs, antibodies (the first domain) with the following variable region sequences exhibit higher affinity to BCMA:

amino acid sequence of any one of SEQ ID NOs.17 and 19-21 in the heavy chain variable region, and amino acid sequence represented by any one of SEQ ID NOs.18 and 22-27 in the light chain variable region;

Based on the above heavy chain variable region and light chain variable region, the amino acid sequences having at least one of the following two features are also within the scope of the present disclosure: a) binding to the same antigenic epitope; and b) having a sequence identity greater than 70%, 80%, 85%, 90%, 97%, 98% or 99%.

Furthermore, antibodies (the first domain) with the following variable region sequences exhibit higher affinity to BCMA:

amino acid sequence represented by SEQ ID NO.17 in the heavy chain variable region, and amino acid sequence represented by SEQ ID NO.18 in the light chain variable region;

Or, amino acid sequence represented by SEQ ID NO.20 in the heavy chain variable region, and amino acid sequence represented by SEQ ID NO.22 in the light chain variable region;

Or, amino acid sequence represented by SEQ ID NO.19 in the heavy chain variable region, and amino acid sequence represented by SEQ ID NO.27 in the light chain variable region;

Or, amino acid sequence represented by SEQ ID NO.21 in the heavy chain variable region, and amino acid sequence represented by SEQ ID NO.25 in the light chain variable region;

Or, amino acid sequence represented by SEQ ID NO.20 in the heavy chain variable region, and amino acid sequence represented by SEQ ID NO.26 in the light chain variable region.

In the bispecific antibodies of the present disclosure, the first domain is an antibody capable of binding to BCMA, consisting of two complete heavy chain-light chain pairs, wherein each pair of light chain and heavy chain is connected by disulfide bonds.

The Fc fragment of the heavy chain of the first domain may be Fc fragment of human or humanized antibodies (IgG1, IgG2, IgA, IgE, IgM, IgG4 or IgD).

As one embodiment of the present disclosure, the Fc fragment of the heavy chain of the first domain is Fc fragment of human or humanized IgG4 antibodies.

As a preferred embodiment of the present disclosure, the heavy chain of the first domain has the amino acid sequence represented by SEQ ID NO.32, and the light chain has the amino acid sequence represented by SEQ ID NO.33.

Or, the heavy chain has the amino acid sequence represented by SEQ ID NO.49, and the light chain has the amino acid sequence represented by SEQ ID NO.42.

Or, the heavy chain has the amino acid sequence represented by SEQ ID NO.50, and the light chain has the amino acid sequence represented by SEQ ID NO.44.

Or, the heavy chain has the amino acid sequence represented by SEQ ID NO.51, and the light chain has the amino acid sequence represented by SEQ ID NO.46.

Or, the heavy chain has the amino acid sequence represented by SEQ ID NO.52, and the light chain has the amino acid sequence represented by SEQ ID NO.48.

These antibodies binding to BCMA have high affinity to BCMA, and can ensure that the functions of both antibodies can be fully exerted when they form bispecific antibodies with antibodies binding to CD3.

On the basis of the above heavy chain and light chain sequences, amino acid sequences having at least one of the following features are also within the scope of the present disclosure: a) binding to the same antigenic epitope; and b) having a sequence identity greater than 70%, 80%, 85%, 90%, 97%, 98% or 99%. The abovementioned human anti-human BCMA antibodies provided by the present disclosure binds to human BCMA with an affinity of 0.2 nM to 10 nM, which inhibit BCMA ligand binding to human BCMA, but can bind to cells expressing BCMA including human multiple myeloma cells or lymphoma cells.

For the second domain binding to CD3 antigen, the heavy chain variable region has the amino acid sequence represented by SEQ ID NO.28, and the light chain variable region has the amino acid sequence represented by SEQ ID NO.29.

Preferably, the light chain variable region and the heavy chain variable region of the second domain are connected by linker peptides to form a single-chain antibody, which has the amino acid sequence represented by SEQ ID NO.31.

The bispecific antibody of the present disclosure is preferably designed with the following structure: the first domain contains two complete light chain-heavy chain pairs, the second domain contains two single-chain antibodies, which are connected in any of the following manners to form the symmetrical structure:

(1) The C-termini of the two single-chain antibodies of the second domain are respectively connected to the N-termini of the two heavy chains of the first domain through linker peptides.

(2) The N-termini of the two single-chain antibodies of the second domain are respectively connected to the C-termini of the two heavy chains of the first domain through linker peptides.

The present disclosure finds that for the sequences of the above-mentioned first domain and the second domain, bispecific antibodies with the above-mentioned symmetrical structure can better retain the specific antigen-binding ability of the original antibody of the first domain and the second domain than those with other structures, with excellent biological function of binding to BCMA and CD3, and obvious advantages in manufacturing technique and pharmaceutical properties. The present disclosure has developed a BCMA- and CD3-binding bispecific antibody with the abovementioned molecular structure, which has a specific targeting effect and can efficiently stimulate a directed immune response to kill tumor cells.

The amino acid sequences of the linker peptides for connecting the first domain and the second domain are preferably $(GGGGX)_n$, wherein X is Gly or Ser, and n is a natural number of 1 to 4.

As a preferred embodiment of the present disclosure, the amino acid sequence of the linker peptide is represented by SEQ ID NO.30.

As an example of bispecific antibodies with the aforementioned structure, the present disclosure provides a bispecific antibody against human CD3 and BCMA. In the structures and sequences of the heavy chain variable region and the light chain variable region of the above-mentioned single-chain antibodies, and the heavy chain and the light chain of monoclonal antibodies, the present disclosure has constructed two bispecific antibodies that can simultaneously bind to CD3 and BMCA, with structures and sequences listed as follows:

(1) The heavy chain of the first domain is connected with the second domain to form a fusion protein with the amino acid sequence represented by SEQ ID NO.34, and the light chain of the first domain has the amino acid sequence represented by SEQ ID NO.33;

(2) The heavy chain of the first domain is connected with the second domain to form a fusion protein with the amino acid sequence represented by SEQ ID NO.35, and the light chain of the first domain has the amino acid sequence represented by SEQ ID NO.33;

(3) The heavy chain of the first domain is connected with the second domain by linker peptides, having an amino acid sequence represented by SEQ ID NO.41, and the light chain has the amino acid sequence represented by SEQ ID NO.42;

(4) The heavy chain of the first domain is connected with the second domain by linker peptides, having an amino acid sequence represented by SEQ ID NO.43, and the light chain has the amino acid sequence represented by SEQ ID NO.44;

(5) The heavy chain of the first domain is connected with the second domain by linker peptides, having an amino acid sequence represented by SEQ ID NO.45, and the light chain has the amino acid sequence represented by SEQ ID NO.46; and (6) The heavy chain of the first domain is connected with the second domain by linker peptides, having an amino acid sequence represented by SEQ ID NO.47, and the light chain has the amino acid sequence represented by SEQ ID NO.48.

The sequences represented by SEQ ID NOs.1-52 disclosed and claimed above comprise "conservative sequence modifications", that is, nucleotide and amino acid sequence modifications that do not significantly affect and change the binding features of antibodies or those containing the indicated amino acid sequence. The conservative sequence modifications include substitutions, additions or deletions of nucleotide or amino acid. The modifications can be introduced into SEQ ID NOs.1-52 by standard techniques in the field, such as site-directed mutagenesis and PCR-mediated mutagenesis. The conservative amino acid substitutions include substitution of an amino acid residue with an amino acid residue having similar side chains or other amino acid residues. In the field, the families of amino acid residues with similar side chains have been defined, consisting of amino acids with basic side chains (such as lysine, arginine, histidine), amino acids with acidic side chains (such as aspartic acid, glutamic acid), and amino acids with uncharged polar side chains (such as glycine, asparagine, glutamine, serine, threonine, tyrosine, cysteine, tryptophan), amino acids with non-polar side chains (such as alanine, valine, leucine, isoleucine, proline, phenylalanine, methionine), amino acids with β-branched side chains (such as threonine, valine, isoleucine), and amino acids with aromatic side chains (eg, tyrosine, phenylalanine, tryptophan, histidine). Therefore, it is preferred to replace a non-essential amino acid residue in a human anti-BCMA antibody with another amino acid residue from the same side chain family.

Therefore, antibodies having the amino acid sequence disclosed above and/or those containing the amino acid sequence disclosed above, including antibodies substantially encoded by similar sequences of conservative sequence modifications, or those containing similar sequences of conservative sequence modifications, are considered to be within the scope of the present disclosure.

The present disclosure also provides nucleic acids encoding the bispecific antibody binding to BCMA and CD3.

Considering the degeneracy of codons, the gene encoding the indicated antibody in the present disclosure can be modified in its coding region without changing the amino acid sequence, to obtain the gene encoding the same antibody. A person skilled in the art can artificially synthesize and modify the gene according to the codon preference of the host expressing the antibody, to improve the expression efficiency of the antibody.

The present disclosure also provides biological materials containing the nucleic acids encoding the bispecific antibodies binding to BCMA and CD3, including recombinant DNA, expression cassette, vector, host cell, engineering bacteria or cell line.

The indicated vectors include but are not limited to cloning vectors and expression vectors and may be plasmid vectors, viral vectors, and transposons.

The indicated host cell or cell line may be a cell or cell line derived from microorganisms or animals.

The present disclosure provides the preparation method of the bispecific antibody binding to BCMA and CD3, which consists of constructing expression vectors containing encoding genes of the first domain and the second domain; introducing the expression vectors into host cells, to obtain host cells expressing the bispecific antibody: culturing the host cell, and obtaining the bispecific antibody through separation and purification.

When preparing the bispecific antibody, a person skilled in the art can select conventional host cells, expression vectors, ways for introducing expression vectors into host cells, and antibody isolation and purification methods as required.

Based on the function of the bispecific antibody binding to BCMA and CD3 provided by the present disclosure, the present disclosure lists any one of the following uses of the bispecific antibody binding to BCMA and CD3 or its encoding nucleic acid or biological materials containing the nucleic acid:

(1) Use in the preparation of medicines for diagnosis, prevention or treatment of BCMA-expressing B cells-related diseases, which preferably consist of B-cell-related tumors (including but not limited to multiple myeloma or lymphoma) and autoimmune diseases caused by B cells;

(2) Use in the preparation of drugs for diagnosis, prevention or treatment of diseases with BCMA as a target, preferably including antineoplastic medicines or medicines against autoimmune diseases;

(3) Use in the preparation of medicines for killing cells expressing BCMA;

(4) Use in the preparation of detection reagents for BCMA and/or CD3;

(5) Use in the preparation of related reagents suitable for CAR-T therapy.

The above-mentioned BCMA-expressing B cells-related diseases are preferably malignant tumors and autoimmune diseases with high expression/overexpression of BCMA.

The bispecific antibody provided by the present disclosure can be used for treatment and diagnosis. Antibodies can be labeled, cross-linked or conjugated and fused with other proteins or polypeptide molecules to form complexes (such as cytotoxic substances, radioactive toxins and/or chemical molecules, etc.) for diagnosis and treatment.

The present disclosure provides multispecific antibodies that contain the indicated bispecific antibody binding to BCMA and CD3, fusion proteins, immunotoxins, medicines or detection reagents.

The above-mentioned immunotoxins comprise the bispecific antibodies connected to cytotoxic agents in various forms.

Various forms of connection refer to antibody being labeled, cross-linked in vitro or conjugated molecularly. The cytotoxic agents include chemical molecules, radioactive isotopes, polypeptides, toxins and other substances that can kill or induce cell death.

The above-mentioned fusion proteins comprise the above-mentioned bispecific antibody provided by the present disclosure and a complex consisting of other proteins or polypeptide molecules with certain functions.

Specifically, the fusion proteins can be recombinant fusion protein molecules obtained with recombinant expression vectors constructed by linking antibody genes with immunotoxin or cytokine genes through mammalian cells or other expression systems.

The above-mentioned medicines and detection reagents may also contain other active ingredients or excipients allowed in the fields of pharmacy and detection reagents (e.g., antibody components and pharmacologically acceptable delivery molecules or solutions. The component for treatment is sterile and can be freeze-dried at low temperature).

The bispecific antibody in the present disclosure can inhibit one or more biological activities induced by BCMA, which acts by blocking the binding of BCMA to its ligands, or by killing cells with high expression of BCMA, or by internalizing the complex formed after binding to BCMA to deplete BCMA on the cell surface. All interfering functions of BCMA antagonists are equally considered as objectives of the present disclosure.

The beneficial effects of the present disclosure are as follows.

The present disclosure uses genetic engineering and phage surface display library technology to screen the specific antibody against human B cell surface antigen BCMA from the library of single-chain antibody with natural fully human sequence. Multiple clones with significantly improved binding ability are obtained through affinity maturation engineering, with affinity to human BCMA between 0.26 nM to 0.31 nM. The apparent affinity measured by flow cytometry is 61 to 97 times higher than that of the parental antibody, confirming that the anti-human BCMA antibody and the optimized mutants in the present disclosure have good binding ability to BCMA.

On this basis, the present disclosure provides a bispecific antibody, which can simultaneously bind to BCMA and CD3, has specific targeting effect, and can efficiently stimulate directed immune responses. The bispecific antibody better retains the biological functions of anti-CD3 antibody and anti-BCMA antibody, which has excellent biological function of simultaneously binding to BCMA and CD3 as a bispecific antibody, forming a bridge between tumor cells and immune effector cells, effectively activating immune effector cells and directed immune responses, significantly enhancing the effects of immune cells in killing tumor cells, and reducing the ADCC effect to the largest extent, with high safety.

The bispecific antibody provided in the present disclosure has a good prospect for treatment, mainly manifested as specific binding to human BCMA and CD3. ELISA and flow cytometry show specific binding to BCMA on the surface of H929 and RPMI8226 cells and T cells, indicating good target specificity. The bispecific antibody has a high target cell-killing efficiency through the in vitro cell-killing efficiency test.

In addition, the bispecific antibody provided in the present disclosure has a completely symmetrical structure, which will not produce protein isomers with other structures when expressed by the host, thereby greatly reducing the difficulty of extraction and purification processes and having advantages of simple preparation and high yield, which shows broad application prospects in tumor immunotherapy.

The present disclosure provides bispecific antibody candidate for the development of anti-tumor antibody medicines targeting BCMA, CAR-T reagents, and the prevention and treatment of other diseases such as B cell-related inflammation and autoimmune disorders. The bispecific antibody in the present disclosure can simultaneously bind to immune cells and tumor cells, guide T-cell immune response, and specifically and effectively kill tumor cells, which can be developed as antibody drugs for multiple myeloma.

DETAILED DESCRIPTION OF THE PREFERRED EMBODIMENT

Figure 1:
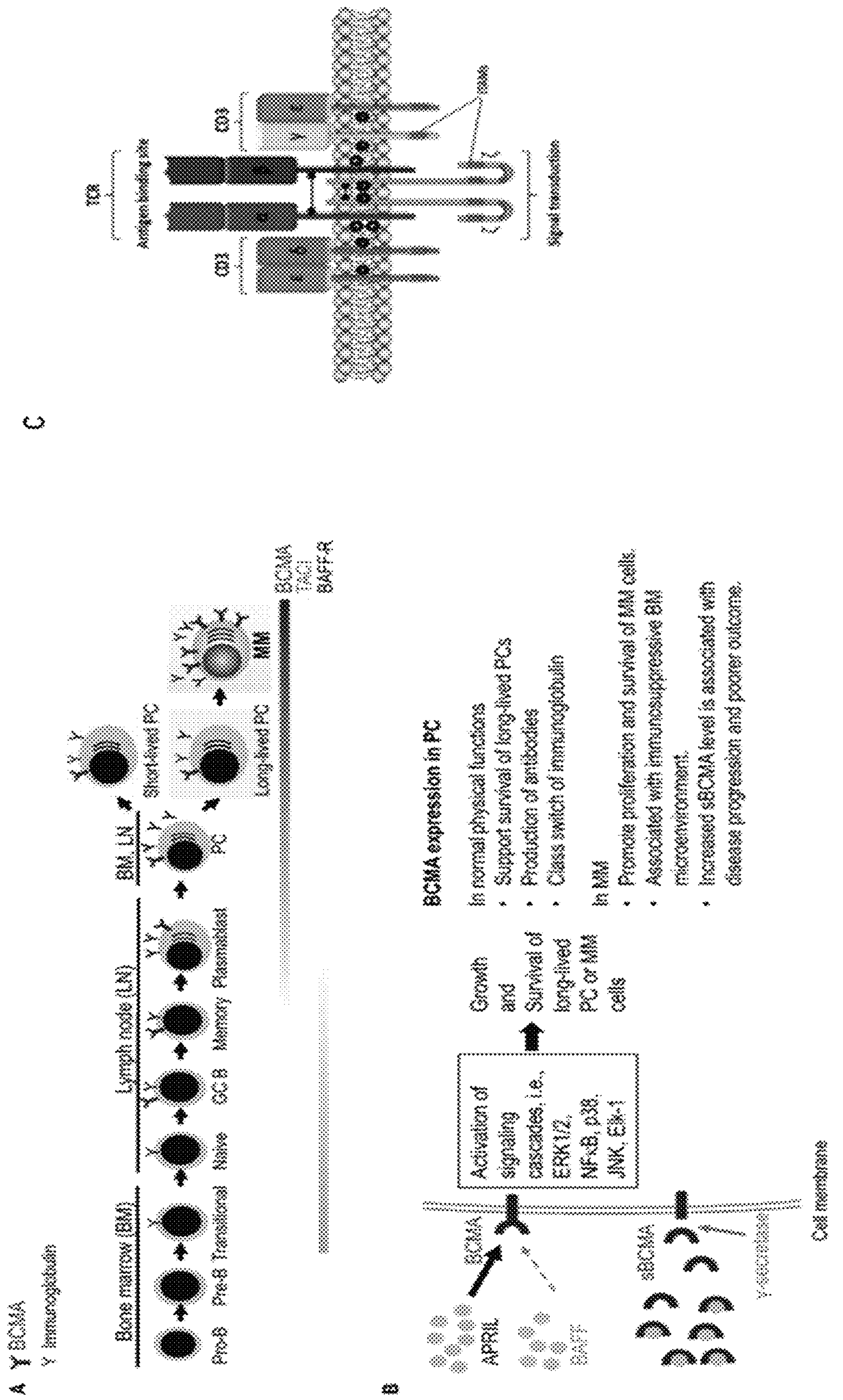
FIG. 1. Schematic diagram of BCMA expression of and TCR structure in the background technology of the present disclosure. (Graph A) Expression of BCMA antigen in the developmental stage of B cells: (Graph B) A signal pathway of ligand action of BCMA antigen, with sources: fimmu-09-01821-g001.jpg (1050×762) (frontiersin.org): (Graph C) Structure of T cell receptor (TCR) complex and composition of CD3, with source: https://www.researchgate.net/publication/299549376.

The following Examples are provided to illustrate the present disclosure but are not intended to limit the scope of the present disclosure.

Example 1: Screening of Anti-Human BCMA Antibody from Natural Human Antibody Phage Surface Display Library Antibody library technology is to clone all antibody variable region genes of a certain animal (including humans) into plasmids or phages, which then infect *Escherichia coli*, leading to expression of antibody fragments on the surface of phage particles, or in the periplasm, and cytoplasm of *Escherichia coli*, then the target antigen is used to screen the clones carrying specific antibody genes from the antibody library, so as to obtain the corresponding specific antibody. Various antibodies needed in basic research and clinical development such as those against tumor-associated membrane protein antigens, autoantigens related to autoimmune diseases, and viral antigens of viral diseases have been screened from the antibody library. These results show the great potential of antibody library technology in basic research and antibody medicine development. In particular, fully human monoclonal antibodies obtained from the human antibody library overcomes the obstacle of getting human monoclonal antibody with mouse hybridoma technology: due to the high conservation of human antibody sequences, these antibodies have much lower immunogenicity to human immune system than those derived from animals, which are accordingly safer.

The non-immune human natural antibody library uses healthy people who are called donors as the source of antibody genes. The immunogenicity of antibodies obtained by using natural human antibody sequences is very low to human immune system. All RNAs were extracted from the donor's peripheral blood mononuclear cells (PBMC) with an RNA extraction kit (such as QIAGEN's RNeasy Mini Kit, catalog number 74104) by using molecular biology and DNA manipulation techniques, and then the same amount of RNAs were extracted from each RNA sample a pooled, to synthesize cDNA of light and heavy chain gene with a reverse transcription kit (such as cDNA synthesis kit of ThermoFisher Scientific, SuperScript™ IV Reverse Transcriptase). With these antibody cDNAs as templates, in the first round of amplification, all member genes of each subgroup were obtained by PCR amplification with subgroup-specific upstream primers and constant region primers. In the second round of PCR, the 3'-terminal primer set of the heavy chain variable region (VH) with bridging and the 5'-terminal primer set of the light chain variable region (VL) with bridging were paired with their respective primers at the other end (containing specific restriction endonuclease sites), allowing the obtained VH and VL to be linked together to form a single-chain antibody (scFv) gene. These scFv genes were cloned into lysogenic phagemid (such as M13 phagemid) vectors to construct an antibody library by using the specific endonuclease sites at the 5'-terminal and 3'-terminal of these single-chain antibody genes. The size of the library reached 5 billion colony forming units (cfu).

Biopanning refers to a process of screening antibodies with specific targets to obtain specific clones. To obtain human BCMA antigen-specific human antibodies, liquid phase screening was used for panning. The general steps of the liquid phase panning are as follows: firstly, the commercialized BCMA antigen (BCMA-Fc fusion protein, Acrobiosystems, catalog number BC7-H5254) was modified with biotin, allowing each molecule to cross-link 3 to 5 biotin molecules, and the free biotin was removed. An appropriate amount of biotin-labeled BCMA antigen was bound to streptavidin-coupled magnetic beads (such as Dynabeads™ M-280 Streptavidin, ThermoFisher Scientific, catalog number 11205D). A human antibody library containing 10 billion phage particles expressing different antibodies was thawed. Both magnetic beads and antibody library were blocked with 4% non-fat dry milk solution (4% MPBS), to eliminate non-specific action sites. Since there may be streptavidin on the magnetic beads that has not been bound by avidin, and the fact that BCMA antigen molecules are fusion proteins composed of human Fc, it is necessary to add a sufficient amount (50-100 times more than the amount of target protein used) of streptavidin and human antibody Fc to the thawed antibody library at the same time, to remove antibody clones that bind them. The blocked antibody library solution and magnetic beads (total volume <1 ml) were added to a 1.5 ml Eppendorf tube and incubated for 2 hours at room temperature with rotational mixing, to allow BCMA-specific phage antibodies to bind. After incubation, the Eppendorf tube was placed on the magnetic rack for 1 minute, to separate the magnetic beads and the solution. A pipette was applied to remove the solution as much as possible, then a new tip was used to replace the used tip, to add 1 ml of washing solution PBST (phosphate buffer solution (PBS) with Tween 20 at a final concentration of 0.05%) to the Eppendorf tube which was kept away from the magnetic rack and then placed on the rack to separate the magnetic beads and the solution after the pipette was applied to gently suspend the magnetic beads. The solution was removed and the process was repeated three times. Then the washing solution was changed to PBS and the magnetic beads were washed 3 times. After washing, most of non-specific and low-affinity phage antibodies were removed, while specific phage antibodies remained on the magnetic beads. Eluent (10 mM Glycine, pH2.0) was added to the magnetic beads, which was then resuspend left at room temperature for 10 minutes, placed on the magnetic rack to separate the magnetic beads and the solution. The solution was drawn into a clean Eppendorf tube, and 1/10 1 M Tris solution (pH8.0) was added to neutralize the solution, obtaining the eluate containing thousands of different phage antibodies that bind to the BCMA antigen, thus the first round of panning was completed.

To further harvest specific antibody clones with high affinity, more rounds of panning are required. To this end, the phage antibody solution eluted from the first round of panning was used to infect *E. coli* (such as TGI strain) in logarithmic phase that can be infected by M13 phage, to obtain an infection solution. A small amount of the solution was taken for serial 10-fold gradient dilutions (usually diluted to one millionth of the stock solution, and the last three gradients were taken for coating) to determine the titer of the output produced in the first round. The titer is also called the maximum diversity of the first round, usually, the output titer after the first round of panning was below 10 E6 cfu. The rest of the infection solution was coated on the bacterial culture plate containing the corresponding antibiotics and cultured overnight, to obtain colonies: the colony layer was scraped off and resuspended with culture medium. Sufficient amount of resuspension liquid containing the diversity of the first round output was taken and added into a shake flask containing sufficient liquid culture medium (2YT-CG, wherein carbenicillin and glucose were added into 2YT culture medium, at final concentration of 100 μg/ml and 2%, respectively). The resuspension liquid was diluted to below 0.1 OD600 and cultured until the logarithmic phase, when OD600 reached about 0.5. To make these antibodies obtained in the first round of panning reappear on the surface of phage particles, 10 ml of bacterial solution was taken and added with helper phage M13K07 to make the multiplicity of infection 20:1. The mixture was kept at 37° C. for 30 minutes (the stage was called phage rescue), then centrifuged, resuspended with 50 ml expression medium (2YT-AK, wherein carbenicillin and kanamycin were added into 2YT culture medium, at final concentrations of 100 μg/ml and 30 μg/ml, respectively), and cultured overnight at 30° C. and 200 rpm. On the following day, the culture supernatant was harvested by centrifugation, and was added with 1/5 volume of PEG8000/NaCl (PEG-8000 20%, NaCl 2.5 M), thoroughly mixed, and incubated on ice for 1 hour. The phage antibody particles were harvested by high-speed centrifugation (11,500×g) for 30 minutes. The precipitates were resuspended with 1 ml PBS solution and centrifuged at high speed to remove bacterial debris. The supernatant was the amplification solution after the first round of panning, wherein each contained antibody clone had been amplified more than ten thousand times. The amplification solution can be used for the second round of panning. The operation of the second round of panning was the same as that of the first round, except that the washing with PBST/PBS was increased to 6 times (6/6). In the third round, the washing frequency can be further increased to 10/10. Multiple rounds of panning usually effectively enrich specific clones, with significantly reduced diversity but high affinity, which is convenient for subsequent monoclonal screening.

To obtain specific monoclonal antibodies, a monoclonal phage enzyme-linked assay (Monophage ELISA) is required. For this purpose, single colonies that were well-separated in the second and/or third round of gradient dilutions were individually inoculated into 96-well culture plates containing 2YT-AG (93 colonies per plate, with three wells as negative control), and cultured overnight, which was the master plate. The bacterial solution in each well of the master plate was inoculated into a new culture plate to grow to the logarithmic phase, and the above-mentioned phage rescue was performed to allow expression of the antibody of each clone on the surface of the phage. The BCMA antigen (1 μg/ml) was coated on a regular 96-well enzyme-linked plate, while human Fc with the same concentration was coated on another enzyme-linked plate. The bacterial solution of each individually expressed monoclonal phage antibody was added to the corresponding wells of the BCMA plate and the Fc plate respectively, followed by appropriate second antibody and horseradish peroxidase (HRP)-conjugated third antibody. The substrate was colored, and the absorbance value (450 nM) was read. The judgment method of BCMA-positive clones was as follows: The clone was negative on the Fc plate (not more than 1.5 times the absorption value of the negative well on the plate where the clone was located), but positive on the BCMA plate (more than 3 times the absorption value of the negative well on the plate where the clone was located), with absorption value of the wells higher than that of the corresponding wells on the Fc plate. Analysis showed that the clones corresponding to 10 wells were only positive for BCMA antigen, and negative for Fc, and the clones were collectively called hit.

The hit bacterial solution was inoculated into 3 ml 2YT-CG from corresponding wells of the master plate and cultured overnight at 37° C. and 200 rpm. On the following day, the phagemid DNA was extracted, and the sequence of the single-chain antibody region containing each hit was determined with specific primers. DNA sequences of the coding regions were translated into amino acid sequences, and multiple sequence alignments (CLUSTALW, website link https://www.genome.jp/tools-bin/clustalw) were performed to determine the clone specificity. Analysis revealed that the ten hits belonged to two different clones in sequence, one of which was named B10, thus obtaining the variable region sequence of a fully human antibody against human BCMA antigen. The amino acid sequences of CDR1, CDR2 and CDR3 in the heavy chain variable region of B10 were represented by SEQ ID NO.4-6 respectively, and those of CDR1, CDR2 and CDR3 in the light chain variable region of B10 were represented by SEQ ID NOs.1-3 respectively: the amino acid sequence of the heavy chain variable region was represented by SEQ ID NO.17, and that of the light chain variable region was represented by SEQ ID NO.18. The amino acid sequence of the single-chain antibody composed of the light chain and heavy chain variable regions of B10 was represented by SEQ ID NO.36.

Example 2: Verification of Antibody Function

To verify whether the obtained BCMA antibody clones bind to the purified BCMA antigen and BCMA expressed on the cell membrane surface, the gene of the B10 single-chain antibody was cloned into the eukaryotic expression vector pFH (prepared by EXCYTE LLC), to obtain the plasmid pFH-B10. In the vector, scFv gene was fused with the Fc gene of human IgG4 to express scFv-Fc protein, which can be affinity purified with protein-A or detected by (HRP or fluorescein) labeled anti-human Fc antibody.

After obtaining the scFv-Fc protein of B10, binding of the antibody to BCMA was tested by Octet RED, confirming the specific binding of B10 to BCMA.

Figure 2:
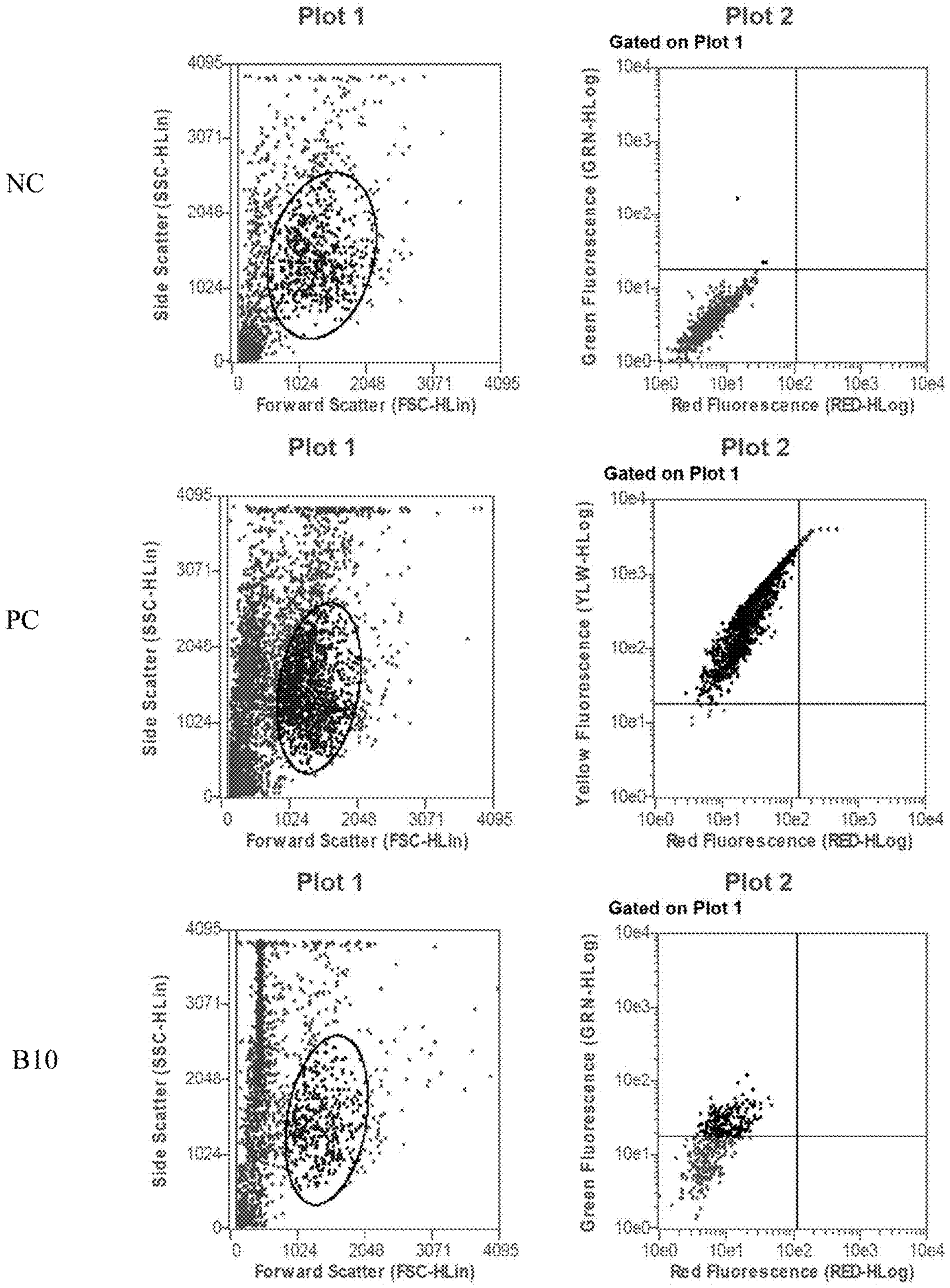
FIG. 2. Analysis of binding of BCMA to clone B10 by flow cytometer (FACS) in Example 2 of the present disclosure. (Top two pictures) Negative control (NC); (two pictures in the middle) Positive control (PC); (Bottom two pictures) Candidate clone B10 (B10).

Binding of B10 to BCMA-expressing cell line H929 (NCI-H929, ATCC® CRL-9068™) was detected by flow cytometry, indicating the specific binding of B10 to the BCMA antigen on the cell membrane surface (see FIG. 2). In the FACS analysis, the percentage in the upper left corner of the four quadrants (positive percentage) represents the binding strength of each single-chain antibody to the cell surface antigen. The positive percentage of clone B10 was 48.96%, verifying the binding ability of the antibody against anti-human BCMA antigen.

Example 3: Antibody Affinity Maturation

The affinity maturation in vitro is a rapid directed molecular evolution operation: mutations were introduced at the DNA level and screening was performed at the protein binding level. For B10 antibodies, in order to avoid introducing mutations that may enhance immunogenicity or structures that may significantly change the antibody, mutation sites were limited to the sequence of the CDR regions, and each position was subjected to saturation mutagenesis separately, with each mutation separately expressed and tested.

The operation process of affinity maturation was as follows: firstly, genes of light and heavy chain variable regions of B10 were respectively cloned into pUFL vectors (pUFL is a plasmid capable of expressing antibody Fab in *E. coli*, prepared by EXCYTE LLC), to obtain Fab form of B10. A full set of primers of single-site random mutations in CDR region was designed, and PCR mutations were performed on each CDR position with site mutation kit (QuikChange Lightning Multi Site-Directed Mutagenesis Kit, Agilent catalog number 210515), BL21 (DE3) competent bacteria were transformed respectively, and monoclonal colonies plates were prepared separately. These mutants were collectively referred to as single site mutation library. Meanwhile, the Fab vector of the B10 parental antibody was also transformed. >30 colonies were selected to prepare DNA for sequence analysis of mutation regions, to evaluate the mutation efficiency. When the mutation efficiency was appropriate (greater than 80%), 92 colonies were selected according to the mutation at each CDR position and added to a 96-well culture plate containing the corresponding culture medium (2YT containing 100 μg/ml Carbenicillin+0.1% glucose), with additional 3 parental colonies chosen, and 3 wells left as blank controls. The plates were placed at 37° C., and cultured at 300 rpm for 6 hours, added with IPTG to a final concentration of 1 mM, transferred to 30° C., and cultured at 300 rpm overnight. Fab fragments were expressed and secreted into the medium.

The conditions of the enzyme-linked reaction were optimized through preliminary experiments, to allow the A450 absorption value of the binding of B10 parental antibody Fab to the antigen BCMA-Fc 3 times higher than the background signal. The BCMA-Fc antigen was coated at 0.25 μg/ml on the enzyme-linked plate one day in advance, and the secreted and expressed mutant Fab was added to the wells on the following day, with HRP-conjugated anti-human Fab as the second antibody, the substrate was colored, and A450 was read, to obtain clones corresponding to the wells with signals 1.5 times higher than the maximum value of the parental wells, and these clones were called hits. All hits of the light and heavy chain variable regions were collected, inducted to express and tested by ELISA to verify their affinity higher than the parental antibody. Sequence analysis of mutant regions of the plasmid of the re-positive clone was performed, to obtain the mutation information of CDR amino acids. The process was called primary screening. All mutation information in the CDR region that was beneficial to the improvement of affinity was obtained: mutation sites that improved affinity in the heavy chain variable region CDR are shown in Table 1, and those in the light chain variable region CDR are shown in Table 2.

TABLE 1

Mutations beneficial to improvement of affinity in the heavy chain variable region CDR of B10

| CDR region position | Parental amino acid | Amino acid with beneficial mutation |
|---|---|---|
| H31 | S | P, K |
| H32 | Y | H, D, G, M, S |
| H33 | A | N |
| H35 | S | H, N, A, M |
| H50 | G | V, T |
| H52 | I | H |
| H53 | I | D, A |
| H54 | F | H |
| H56 | T | K |
| H98 | F | L |

TABLE 2

Mutations beneficial to improvement of affinity in the light chain variable region CDR of B10

| CDR region position | Parental amino acid | Amino acid with beneficial mutation |
|---|---|---|
| L28 | S | N, R, T |
| L97 | L | Q, V, A |
| L98 | I | S, A, R, P |
| L100 | Y | M, L, W, T |
| L101 | V | L, Q |

After screening and obtaining the information of all single mutations beneficial to the improvement of affinity in the entire CDR region from the primary library through ELISA, new multi-site mutation primers were redesigned to include major beneficial mutations, and mutation library was constructed again with the point mutation kit, which was called the combinatorial library. In order to screen all mutation combinations in the light and heavy chain variable regions as much as possible, combinatorial libraries containing multiple mutations in the light and heavy chain variable regions were respectively constructed and screened. The top 5 clones with the highest affinity in the combinatorial library of the light chain variable region were obtained, whose amino acid sequences of the light chain variable region contained five mutant sequences that are represented by SEQ ID NOs.22-26, and CDR1 in the light chain variable region had the amino acid sequence represented by any one of SEQ ID NOs.1 and 12, CDR2 in the light chain variable region had the amino acid sequence represented by SEQ ID NO.2, and CDR3 in the light chain variable region had the amino acid sequence represented by any one of SEQ ID NOs.3, 13, 14, 15, or 16.

The amino acid sequences of the top three clones with the highest affinity in the combinatorial library of the heavy chain variable region were obtained with ELISA screening of the combinatorial library of the heavy chain variable region, whose amino acid sequences of the heavy chain variable region contained three mutant sequences that were represented by the sequences SEQ ID NOs.19-21 respectively, the CDR1 in the heavy chain variable region had the amino acid sequence represented by any one of SEQ ID NOs.7, 8, and 9, and CDR2 in the heavy chain variable region had the amino acid sequence represented by SEQ ID NO.10, and CDR3 in the heavy chain variable region had the amino acid sequence represented by SEQ ID NO.11.

DNAs of the top 5 clones with the highest affinity of the light and heavy chain variable regions were mixed respectively and assembled into the final single-chain antibody combinatorial library by enzyme digestion and linking recombination. The library was screened to select the top 10 with the highest signals, and their DNA sequences were analyzed, obtaining four different single-chain antibody clones, with the corresponding amino acid sequences represented by SEQ ID NOs.37-40.

Figure 3:
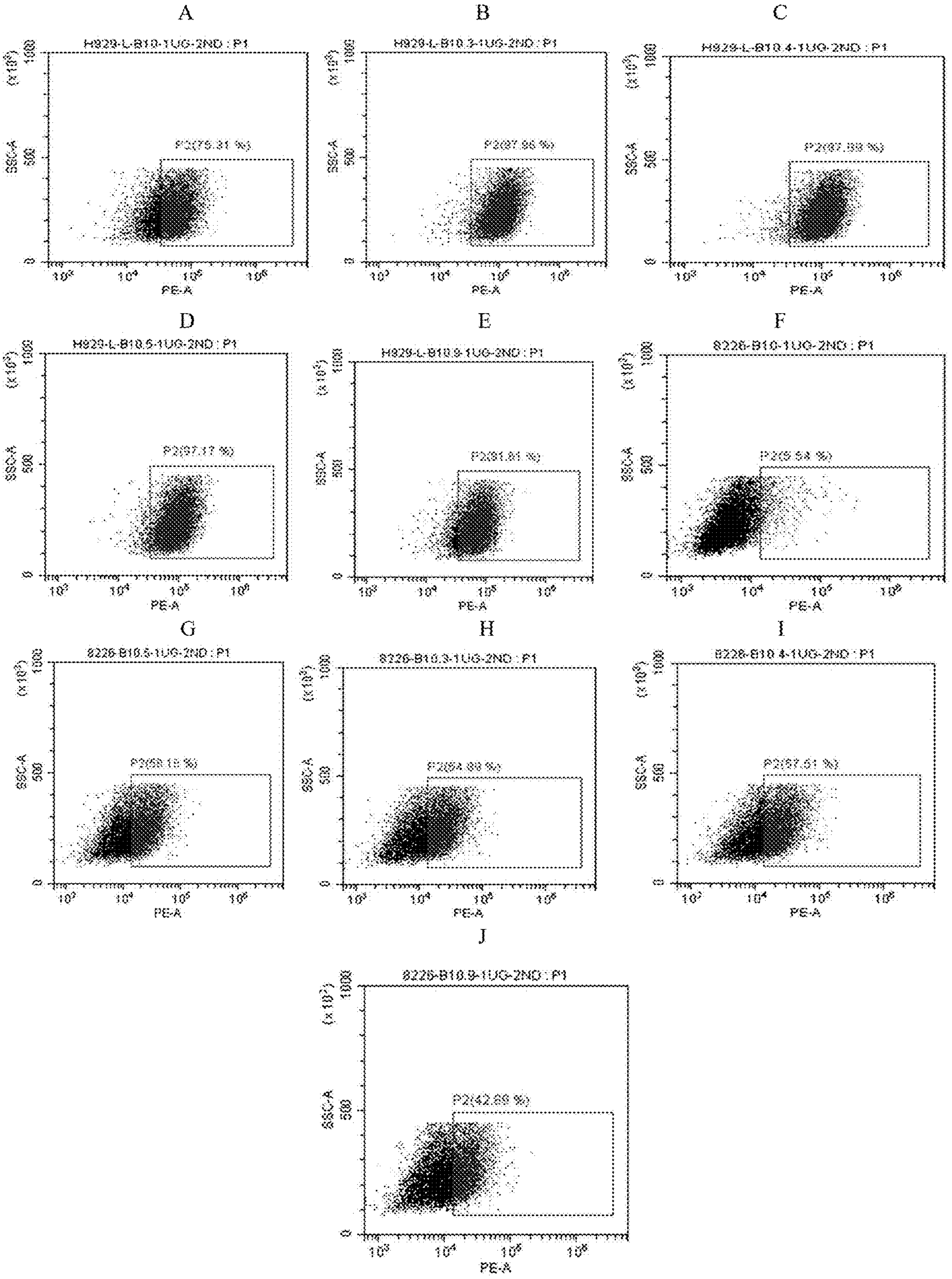
FIG. 3. Analysis of binding of B10 and its affinity matured mutants by flow cytometry in Example 3 of the present disclosure. (Graphs A, B, C, D, and E) B10, B10.3, B10.4, B10.5 and B10.9 binding to H929 cells; (Graphs F, G, H, I, J) B10, B10.3, B10.4, B10.5 and B10.9 binding to RPMI8226 cells.

To check whether the affinity of obtained mutants had been improved, the B10 parental antibody and fusion proteins of the finally obtained 4 mutants B10.3, B10.4, B10.5, B10.9 (amino acid sequences represented by SEQ ID NO.37-40) with Fc (i.e., scFv-Fc) were respectively expressed and purified. The purified products were detected by flow cytometry on two BCMA-positive cell lines H929 and RPMI8226 with different expression levels. The percentages of binding to H929 cells were: 75.31% for B10 parental antibody, increasing to 97.96% for mutant B10.3, improving to 97.89% for mutant B10.4, increasing to 97.17% for mutant B10.5, and improving to 91.61% for mutant B10.9. The percentages of binding to RPMI8226 cells were: 5.54% for B10 parental antibody, increasing to 54.89% for mutant B10.3, improving to 57.51% for mutant B10.4, increasing to 58.18% for mutant B10.5, and improving to 42.89% for mutant B10.9. Results showed that all four mutants had significantly improved binding to BCMA compared to B10 (see Figure. 3).

In order to understand the affinity of B10 and its derived antibodies, the B10 parental antibody and the 4 mutants finally obtained were compared with the BCMA antibody J6 which had known affinity (i.e., clone J6 M0, whose affinity was about 0.2 nM according to the record of patent [WO2012163805A1]) by ELISA respectively. After antibodies with different concentrations were coated on enzyme-linked plates, the biotinylated BCMA antigen, streptavidin-conjugated horseradish peroxidase (HRP) and chromogenic substrate were added step by step. The obtained signal-antibody gradient curve is shown in Graph A of FIG. 4, and the relative affinity change fold is shown in Table 3.

TABLE 3

Binding of B10 and its affinity matured mutants to BCMA tested by ELISA

| Ab | J6 | B10 | B10.3 | B10.4 | B10.5 | B10.9 |
|---|---|---|---|---|---|---|
| EC50 | 26.54 | n/a | 34.3 | 41.12 | 35.78 | 37.94 |
| Fold of J6 | 1.00 | n/a | 1.29 | 1.55 | 1.35 | 1.43 |
| nM | 0.20 | n/a | 0.26 | 0.31 | 0.27 | 0.29 |

Results showed that in terms of intrinsic affinity, the S-curve was not obtained since the binding of B10 parental antibody to human BCMA was significantly weaker than that of J6, and its affinity value could not be generated. In addition, the affinity of B10.3 was about 0.26 nM, B10.4 about 0.31 nM, B10.5 0.27 nM, and B10.9 about 0.29 nM.

Figure 4:
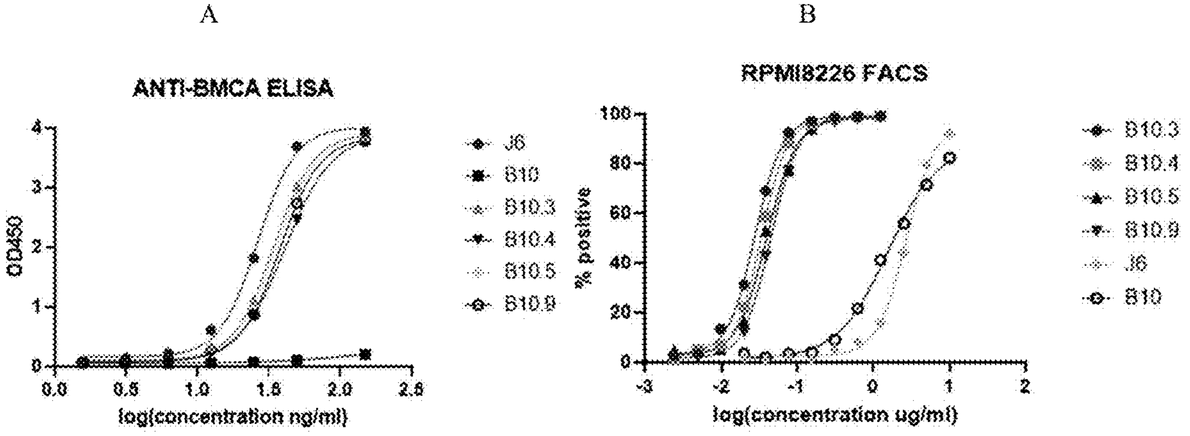
FIG. 4. Comparison of binding of J6, B10 and its mutants by ELISA and flow cytometry in Example 3 of the present disclosure. (Graph A) ELISA. (Graph B) FACS.

In order to understand the apparent affinity of these antibodies to BCMA on the cell surface, the binding of B10 parental antibody and the finally obtained 4 mutants to BCMA-expressing cell line RPMI8226 were compared with J6 by flow cytometry (see Graph B of FIG. 4, Table 4). Results showed that at the cellular level, EC50 of the B10 parental antibody (2.741 μg/ml) was about 1.5 times higher than that of J6 (1.575 μg/ml). EC50s of B10.3, B10.4, B10.5 and B10.9 were 0.02822 μg/ml, 0.03429 μg/ml, 0.04063 μg/ml and 0.04514 μg/ml, respectively. Compared with J6, the fold increase of EC50 of these mutants with improved affinity was 97.13, 79.94, 67.46 and 60.72, respectively.

TABLE 4

Binding of B10 and its mutants to RPMI8226 cell line measured by FACS

| Antibody | B10.3 | B10.4 | B10.5 | B10.9 | J6 | B10 |
|---|---|---|---|---|---|---|
| EC50 (μg/ml) | 0.02822 | 0.03429 | 0.04063 | 0.04514 | 2.741 | 1.575 |
| Fold increase relative to J6 | 97.13 | 79.94 | 67.46 | 60.72 | 1 | 0.57 |

Example 4: Design of BCMA×CD3 Bispecific Antibody

In the present Example, the bispecific antibody was designed with the tumor cell surface antigen BCMA and the immune cell surface antigen CD3 as targets.

Figure 5:
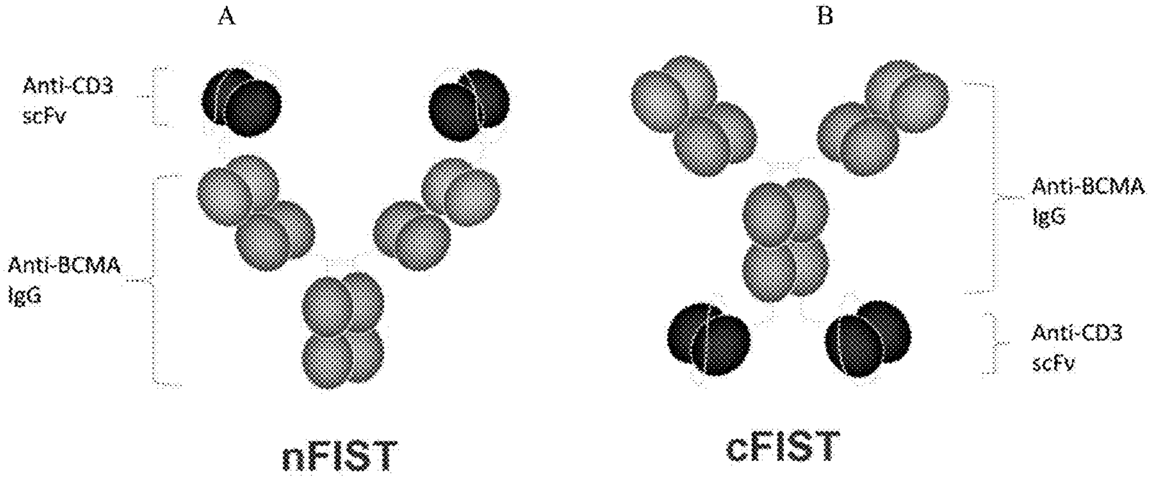
FIG. 5. Schematic diagram of structure of anti-BCMA×CD3 bispecific antibody constructed based on the FIST platform in Example 4 of the present disclosure. (Graph A) A bispecific antibody constructed by N-terminal fusion (nFIST): an anti-CD3 single-chain antibody fused to the N-terminus of anti-BCMA antibody VH. (Graph B) A bispecific antibody constructed by C-terminal fusion (cFIST): an anti-CD3 single-chain antibody fused to the C-terminus of anti-BCMA antibody Fc.

Combining protein structure design software and many manual experimental screening, the present disclosure screened and determined the bispecific antibodies with symmetrical structures including single-chain antibody units and monoclonal antibody units from a variety of bispecific antibodies binding to BCMA and CD3. The technical platform is referred to as FIST (fusion of IgG and scFv technology) in the present disclosure. For example, anti-BCMA monoclonal antibody units can be used as IgG antibodies, including 2 complete light chain-heavy chain pairs (i.e., containing complete Fab and Fc domains, and the heavy and light chains were connected by disulfide bonds); and anti-CD3 can be used as single-chain antibody units, including 2 single-chain antibodies (ScFvs). A linker peptide (SEQ ID NO.30) was used to connect the single-chain antibody and the monoclonal antibody. The single-chain antibody and the monoclonal antibody related to the following method to obtain bispecific antibodies with a symmetrical structure (FIG. 5):

The C-terminus of the single-chain antibody was linked to the N-terminus of the heavy chain variable region (VH) of the monoclonal antibody, to obtain nFIST (Graph A of FIG. 5). The single-chain antibody can also be fused to the C-terminus of IgG-Fc by a linker peptide, to obtain cFIST (Graph B of FIG. 5).

In the present Example, the variable region sequence of the anti-CD3 single-chain antibody UCHT1 was derived from literature (Beverley, P. C. & Callard, R. E. Distinctive functional characteristics of human "T" lymphocytes defined by E rosetting or a monoclonal anti-T cell antibody (1981) Eur. J. Immunol. 11, 329-334) and was humanized (Shalaby et. al., Development of humanized bispecific antibodies reactive with cytotoxic lymphocytes and tumor cells overexpressing the HER2 protooncogene. (1992) J Exp Med. January 1; 175 (1): 217-25). The constructed single-chain antibody was named K3 (SEQ ID NO.31), containing two cysteines (Cys) inserted in the heavy chain and light chain variable regions respectively, which forms a pair of interchain disulfide bond after folding, with the amino acid sequence of the heavy chain variable region represented by SEQ ID NO.28, and that of the light chain variable region represented by SEQ ID NO.29.

Example 5: Preparation of BCMA×CD3 Bispecific Antibody

The bispecific antibody coding genes in the form of nFIST or cFIST were designed according to Example 4, and cloned into the expression vector pG4HK, to obtain two bispecific antibodies K3B10.3 and B10.3K3. Their amino acid sequences of the heavy chains were represented by SEQ ID NO.34 and 35, respectively (fusion peptide formed by connecting the heavy chain of the monoclonal antibody with the single-chain antibody through a linker peptide): with the amino acid sequence of the light chain represented by SEQ ID NO.33. The expression plasmids corresponding to K3B10.3 and B10.3K3 were stably transfected into CHO-K1, respectively, to prepare bispecific antibody proteins.

Figure 9:
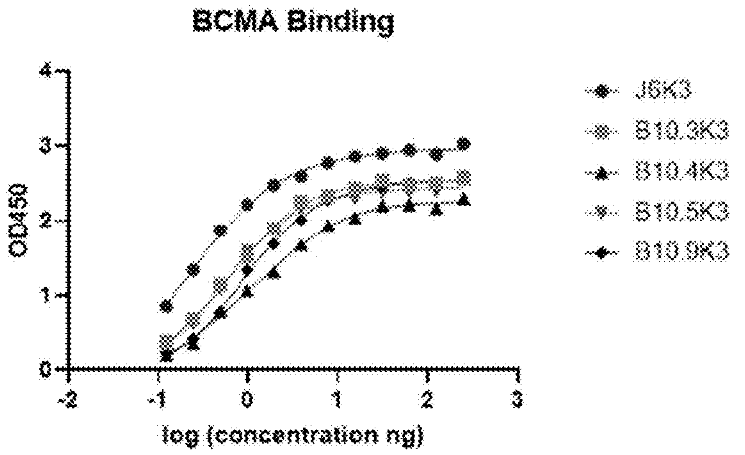
FIG. 9. Killing of BCMA-expressing cells RPMI8226 by T cells mediated through binding of cFIST bispecific antibody to BCMA antigen in Example 7 of the present disclosure. (Graph A) ELISA binding of mutant B10 with improved affinity to BCMA antigen, wherein the antibody is coated at 200 ng/well, biotin-BCMA is subjected to serial half dilution with an initial concentration of 250 ng/ml. (Graph B) Mediated killing of BCMA-expressing cells by mutant B10 with improved affinity, wherein high and low concentrations of B10K3 are tested in experiments, and the standard S-curve is not obtained at low concentration (B10K3), but formed at high concentration (B10K3 (high)), and the EC50 value is calculated according to the curve.
Figure 9:
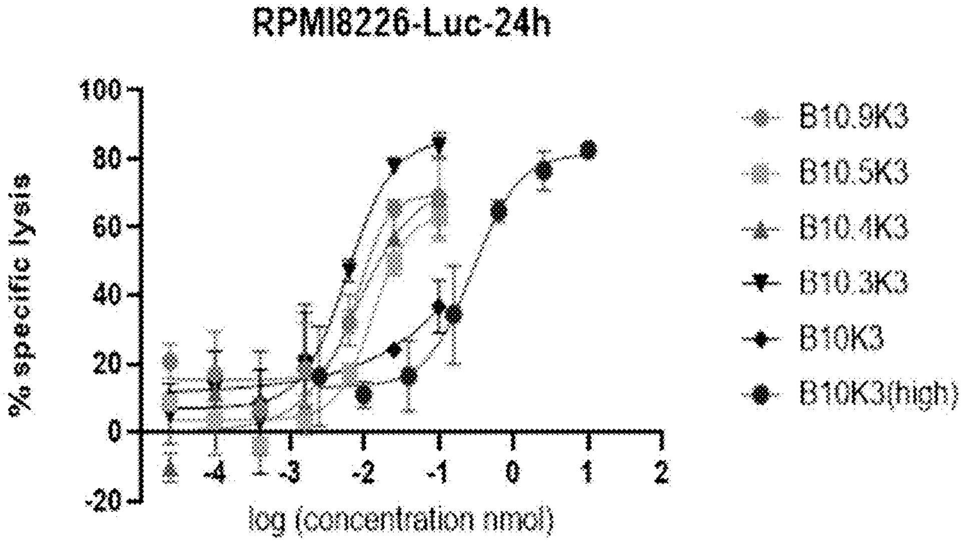

More anti-BCMA×CD3 bispecific antibodies were constructed using the form of cFIST. The heavy chain variable region of the BCMA-binding IgG unit was derived from SEQ ID NOs.17-21; while the light chain variable region of the BCMA-binding IgG unit was derived from SEQ ID NOs.18, 22, or 25-27. Plasmids of these antibodies were transfected into 293F cells, to prepare by transient expression and one-step purification of protein-A, to obtain B10K3 (the amino acid sequence of the heavy chain represented by SEQ ID NO.41; that of the light chain represented by SEQ ID NO.42), B10.3K3, B10.4K3 (the amino acid sequence of the heavy chain represented by SEQ ID NO.43; that of the light chain is represented by SEQ ID NO.44), B10.5K3 (the amino acid sequence of the heavy chain represented by SEQ ID NO.45; that of the light chain represented by SEQ ID NO.46), and B10.9K3 (the amino acid sequence of the heavy chain represented by SEQ ID NO.47; that of the light chain represented by SEQ ID NO.48). SDS-PAGE purity analysis showed monomer purity above 90%. Tests of their binding to BCMA antigen is shown in Graph A of FIG. 9.

The above-mentioned bispecific antibodies were processed with the following steps, to obtain high-purity bispecific antibodies. (1) Material liquid pretreatment: The supernatant of fermentation culture was centrifuged at 2,000 rpm for 10 min, and then filtered with a 0.22 μM filter membrane. (2) Affinity chromatography: MabselectSuRe affinity chromatography column (purchased from GE Company, Cat. No. 18-5438-02) was utilized to capture antibodies in the pretreated fermentation broth, which were passed through the affinity chromatography column after fully balancing the column with the equilibration buffer (10 mM PB, 0.1 M NaCl, pH 7.0), and eluted with elution buffer (0.1 M citric acid, pH 3.0). (3) Cation exchange chromatography: Samples prepared by affinity chromatography was further purified by molecular sieve exchange chromatography, with buffer solution (50 mM PBS, 0.2 Man $Na_2SO_4$, pH 6.7).

Figure 6:
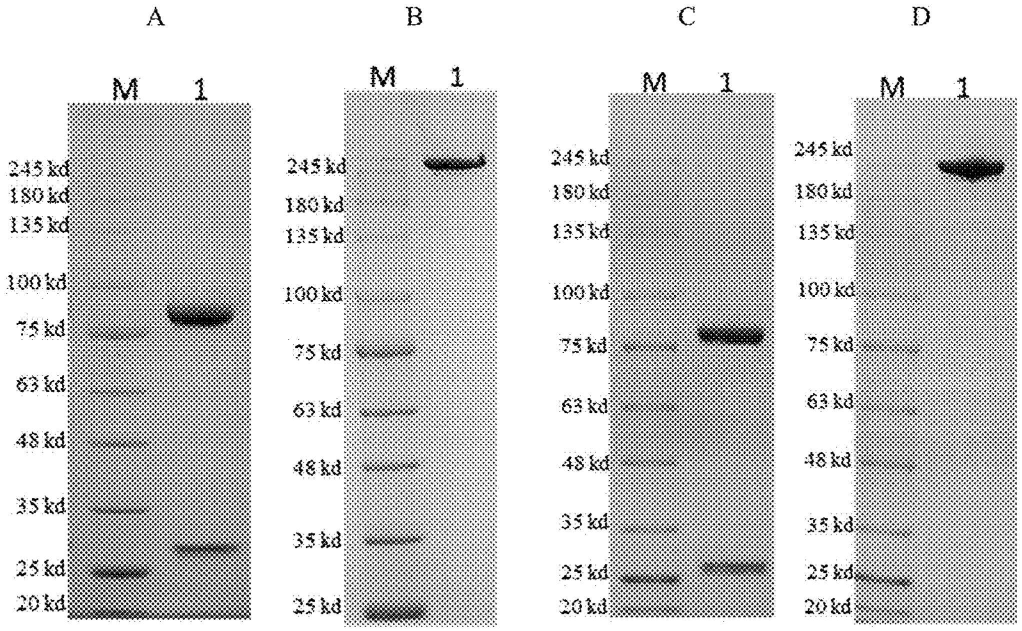
FIG. 6. SDS-PAGE electrophoretogram of bispecific antibodies K3B10.3 and B10.3K3 in Example 5 of the present disclosure. (Graphs A and C) Reducing SDS-PAGE electrophoresis. (Graphs B and D) Non-reducing SDS-PAGE electrophoresis. (Graphs A and B) SDS-PAGE electrophoresis results of K3B10.3 bispecific antibody. (Graphs C and D) SDS-PAGE electrophoresis results of B10.3K3 bispecific antibody. (Lane M) Protein molecular weight standard. (Lane 1) Target protein.
Figure 7:
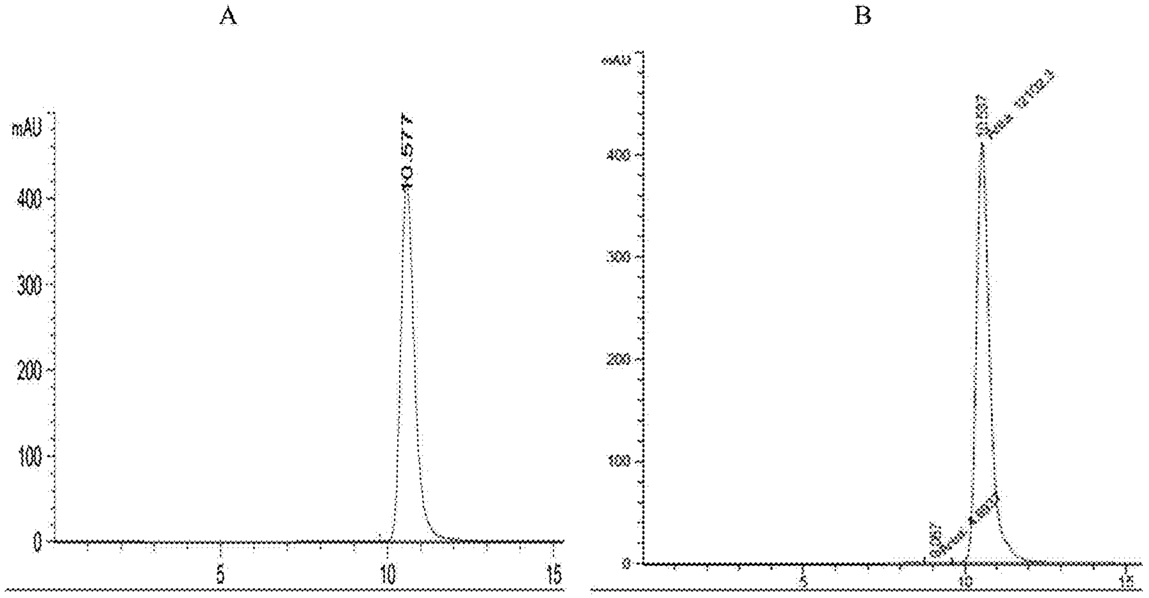
FIG. 7. Peak profile of HPLC-SEC purity analysis of purified bispecific antibodies K3B10.3 and B10.3K3 in Example 5 of the present disclosure. (Graph A) Bispecific antibody K3B10.3. (Graph B) Bispecific antibody B10.3K3.

K3B10.3 and B10.3K3 were tested by SDS-PAGE and HPLC-SEC, and results of SDS-PAGE are shown in FIG. 6. Results of the reducing SDS-PAGE electrophoresis of K3B10.3 are shown in Graph A of FIG. 6, those of non-reducing SDS-PAGE electrophoresis are demonstrated in Graph B of FIG. 6: Result of the reducing SDS-PAGE electrophoresis of B10.3K3 are shown in Graph C of FIG. 6, and those of non-reducing SDS-PAGE electrophoresis are demonstrated in Graph D of FIG. 6. Results of HPLC-SEC are shown in FIG. 7. Result of K3B10.3 are demonstrated in Graph A of FIG. 7, those of B10.3K3 are shown in B of FIG. 7. Results revealed that the bispecific antibodies K3B10.3 and B10.3K3 were successfully prepared through expression and purification, and the monomer purity of the purified bispecific antibodies was above 95%.

Example 6: Binding Activity of Bispecific Antibodies to T Cells Tested by Flow Cytometry PBMC cells of healthy human donors were collected, T cells were purified, resuspended in PBS at $1\times10^6$ cells/reaction tube, rinsed once with 1 ml binding buffer (PBS containing 0.5% w/v BSA+2 mM EDTA), centrifuged (350×g, 4° C., 5 min), and then resuspended in 200 μl of binding buffer. The bispecific antibodies K3B10.3 and B10.3K3 were added to 5 μg/ml respectively and incubated on ice for 45 minutes. Cells were rinsed once as above and resuspended in 100 μl of binding buffer. 5 μl fluorescence labeled secondary antibody (PE anti-human IgG Fc Antibody, Biolegend, 409304) was added to the sample tube, the isotype control (PE Mouse IgG2a, K Isotype Ctrl (FC) Antibody, Biolegend, 400213) was added to the isotype control tube, both were incubated on ice in the dark for 15 min. Cells were rinsed once as above. Cells were resuspended in 200 μl of PBS, and then tested on the machine (Beckman).

Figure 8:
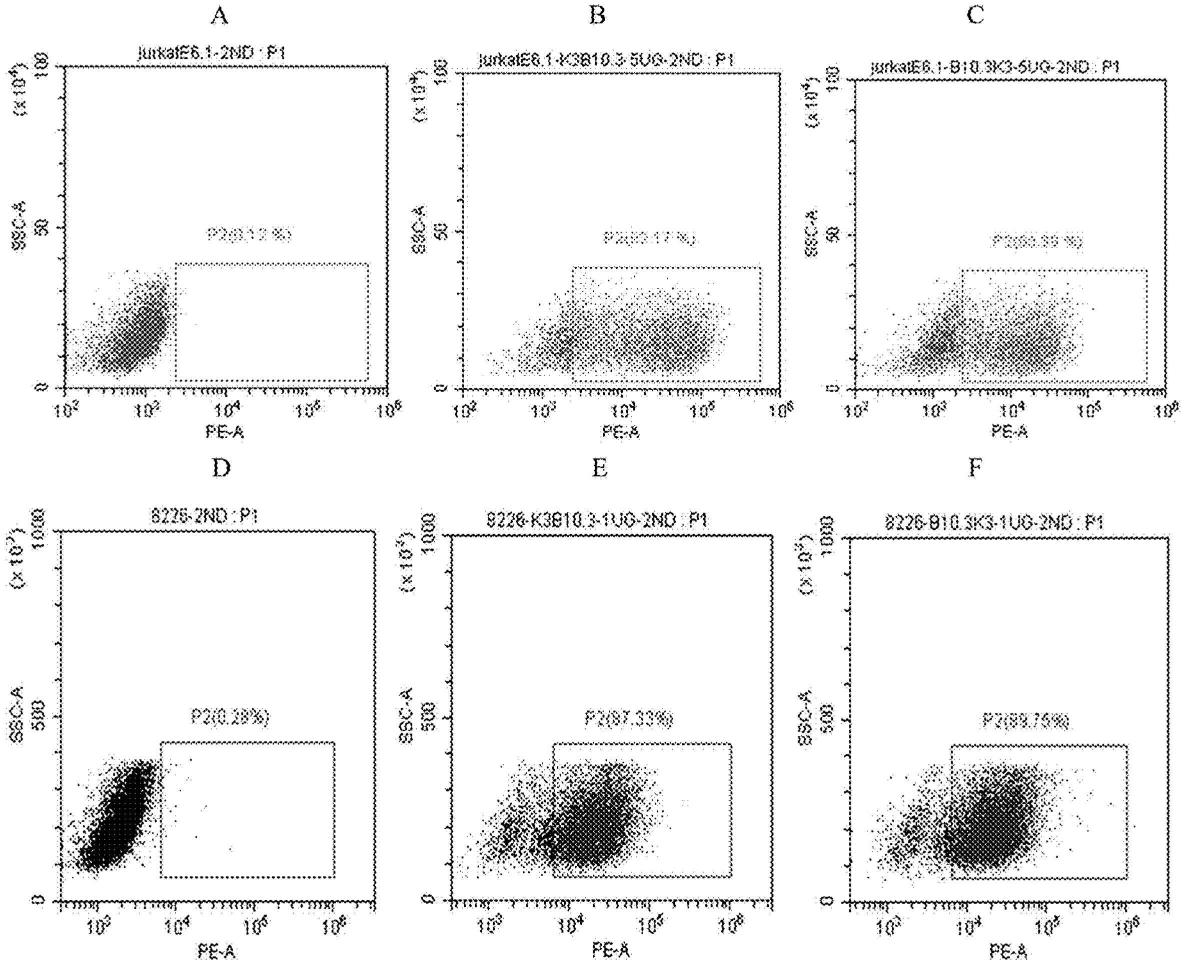
FIG. 8. Analysis of binding of K3B10.3 and B10.3K3 to human Jurkat T cells and RPMI cells in Example 6 of the present disclosure. (Graph A) Bispecific antibody control. (Graph B) K3B10.3. (Graph C) B10.3K3 binding to CD3. (Graph D) Bispecific antibody control. (Graph E) K3B10.3. (Graph F) B10.3K3 binding to BCMA.

Results of binding of K3B10.3 and B10.3K3 to human T cells tested by flow cytometry are shown in FIG. 8, and results of the control are demonstrated in Graph A of FIG. 8, those of binding of K3B10.3 to T cells are shown in Graph B of FIG. 8, and results of binding of B10.3K3 to T cells are demonstrated in Graph C of FIG. 8. Results showed that both bispecific antibodies K3B10.3 and B10.3K3 could specifically bind to T cells, indicating that the bispecific antibody fusion proteins retained the binding function of anti-CD3 single-chain antibody.

To test the binding of anti-BCMA unit to BCMA, T cells in the experiment were replaced with RPMI8226 (ATCC® CCL-155) to perform a similar FACS experiment. Results of the control are shown in Graph D of FIG. 8, and those of K3B10.3 and B10.3K3 are demonstrated in Graphs E and F of FIG. 8.

Example 7: Detection of Cell-Killing Efficiency Mediated by Bispecific Antibodies in Vitro In the present Example, H929-luc and RPMI8226-Luc were used as targeted cells, and PBMC was utilized as immune effector cell to test the targeted cell-killing effect mediated by bispecific antibodies B10K3, B10.3K3, B10.4K3, B10.5K3, B10.9K3 and K3B10.3, with specific experimental steps as follows:

1). Targeted cell preparation: H929-luc and RPMI8226-Luc (luciferase-labeled H929 and RPMI8226 cells prepared in the laboratory) cells were cultured, the targeted cells were evenly mixed by pipetting up and down and then counted, centrifuged at 1000 rpm for 5 min, and washed once with PBS. After the targeted cells were centrifuged and washed, the density was adjusted to $0.2\times10^6$/ml with GT-T551 medium, and 50 μl of the cells were added to each well, as a result, there were 10,000 cells in each well.

2). PBMC preparation: PBMC was used as the effector cell. PBMCs frozen in the liquid nitrogen tank were taken out and thawed (refer to cell cryopreservation and resuscitation), added into a 15 ml centrifuge tube containing PBS or GT-T551 medium, centrifuged at 1,000 rpm for 5 min, and washed twice with PBS or GT-T551 medium. The cell count, activity and density were recorded. The viable cell density was adjusted to $2\times10^6$/ml, and 50 μl of the cells were added to each well, as a result, there were 100,000 cells in each well.

3). Antibody dilution: GT-T551 medium was used to dilute bispecific antibodies B10K3, B10.3K3, B10.4K3, B10.5K3, B10.9K3 and K3B10.3 and B10.3K3, respectively, and the initial antibody concentration was adjusted to 10 nM. Antibodies were diluted in a ratio of 1:5, and 100 μl of the diluted antibodies were added to the cells prepared above, mixed well, and the 96-well plate was put back into the incubator, to detect the killing effect after 18 hours.

4). Detection: Given that H929 or RPMI8226 targeted cells carries the luciferase gene, LUMINEX method was used to test the killing efficiency on the target cells.

With Steady-GLO (Promega company) as the substrate, the buffer in the kit was thawed and added to the substrate powder, mixed well, and divided into 5 ml or 10 ml each tube to complete the reconstruction of Steady-GLO substrate. After the co-cultured cells were evenly mixed by pipetting up and down, 100 μl of the cells were transferred to an opaque white plate, then 100 μl of the reconstructed Steady-GLO substrate was added, and mixed by patting gently, left for 5 minutes before reading the plate. The instrument used for detection was Synergy HT.

5). Data processing: the formula for calculating targeted cell killing ratio is as follows:

Target cell killing ratio (percentage)=100×(the number of wells with only targeted cells−the number of wells tested)/the number of wells with only targeted cells The antibody concentration corresponding to the target cell killing ratio in all tested wells was converted to log 10, which was used as the horizontal axis with the cell killing ratio as the vertical axis to plot a curve. The killing concentration-gradient curves of the bispecific antibodies B10K3, B10.3K3, B10.4K3, B10.5K3, B10.9K3 in the form of cFIST against the sensitive cell line RPMI8226 are shown in Graph B of FIG. 9; the cell killing percentage across gradients is demonstrated in Table 5.

Figure 10:
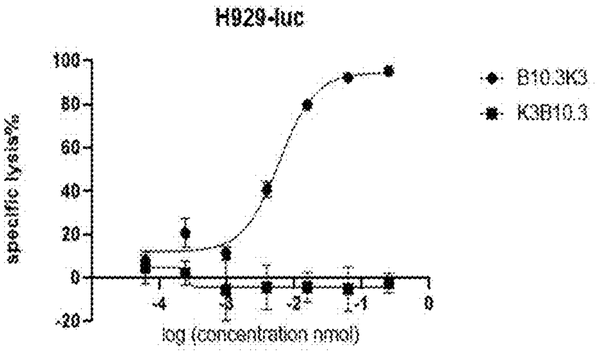
FIG. 10. Diagram of killing of cells with different BCMA expression by T cells mediated through BCMA bispecific antibody in Example 7 of the present disclosure. (Graph A) H929 cells. (Graph B) RPMI8226 cells.
Figure 10:
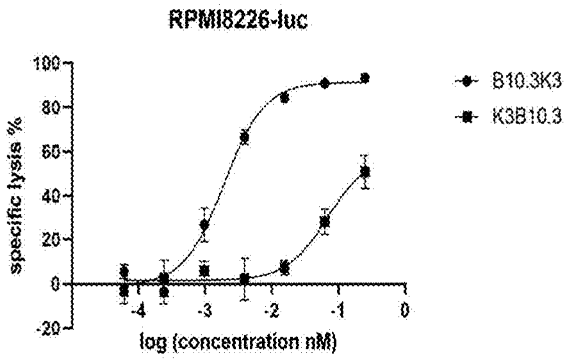

Results of K3B10.3 and B10.3K3 are shown in FIG. 10; their RPMI8226-killing percentages are demonstrated in Table 6; and their H929-killing percentages are shown in Table 7. Results revealed that the bispecific antibody B10.3K3 could effectively mediate the killing of tumor cell lines H929 or RPMI8226 by PBMC, and individual B10.3K3 molecule had the biological functions of both anti-BCMA and anti-CD3 monoclonal antibodies. The efficacy of K3B10.3-mediated killing of target cell RPMI8226 was significantly weaker than that of B10.3K3, especially K3B10.3 showed almost no killing effect on H929 cells. EC50 of target cell-killing mediated by B10.9K3, B10.5K3, B10.4K3, B10.3K3, and B10K3 was 8.759 pM, 12.87 pM, 7.839 pM, 5.833 pM, and 281.7 pM, respectively.

TABLE 5

Target cell killing ratio of killing of target cells RPMI8226 mediated by BCMA/CD3 bispecific antibodies at different concentrations

| nM | B10.9K3 | | B10.5K3 | | B10.4K3 | | B10.3K3 | | B10K3 | |
|---|---|---|---|---|---|---|---|---|---|---|
| 0.1 | 60.77 | 77.35 | 58.20 | 67.98 | 69.81 | 67.41 | 81.10 | 86.51 | 31.27 | 42.02 |
| 0.025 | 66.27 | 64.55 | 51.07 | 49.06 | 64.78 | 49.36 | 78.84 | 76.85 | 25.86 | 22.70 |
| 6.3E−03 | 29.95 | 34.52 | 19.11 | 14.87 | 38.00 | 27.48 | 49.61 | 44.83 | 17.23 | 16.54 |
| 1.6E−03 | 8.96 | 27.99 | 6.96 | 0.38 | 5.35 | 9.98 | 7.65 | 32.26 | 11.37 | 30.92 |
| 3.9E−04 | 9.02 | 4.55 | −3.91 | −21.11 | −34.55 | 7.37 | −7.61 | 13.98 | −2.14 | 19.17 |
| 9.8E−05 | 16.80 | 17.22 | 2.67 | 4.17 | −1.28 | 24.16 | 12.50 | 12.63 | 9.71 | 21.37 |
| 2.4E−05 | 17.22 | 24.38 | 8.43 | 8.44 | −13.27 | −7.27 | 11.57 | −0.91 | 11.12 | 9.26 |

TABLE 6

Target cell killing ratio of killing of target cells RPMI8226 mediated by bispecific antibodies K3B10.3 and B10.3K3 at different concentrations.

| nM | B10.3K3 | | K3B10.3 | |
|---|---|---|---|---|
| 0.25 | 94.65 | 92.04 | 45.57 | 56.19 |
| 6.25E−2 | 92.31 | 89.86 | 32.15 | 24.14 |
| 1.6E−2 | 85.84 | 82.86 | 5.09 | 9.70 |
| 3.9E−3 | 68.89 | 64.42 | −4.47 | 8.82 |
| 9.8E−4 | 21.16 | 32.04 | 2.84 | 8.87 |
| 2.4E−4 | −7.47 | 0.18 | −3.36 | 8.32 |
| 6.1E−05 | 7.71 | 3.14 | −7.30 | 0.84 |

TABLE 7

Target cell killing ratio of killing of target cells H929 mediated by bispecific antibodies K3B10.3 and B10.3K3 at different concentrations.

| nM | B10.3K3 | | | K3B10.3 | | |
|---|---|---|---|---|---|---|
| 0.25 | 94.84 | 95.57 | 95.57 | −4.98 | 2.87 | −4.89 |
| 6.25E−2 | 91.26 | 93.06 | 93.06 | −15.44 | 4.71 | −4.70 |
| 1.6E−2 | 80.60 | 79.11 | 79.11 | −11.72 | 1.69 | −2.78 |
| 3.9E−3 | 36.72 | 42.99 | 42.99 | −0.38 | 3.37 | −15.90 |
| 9.8E−4 | 7.81 | 13.06 | 13.06 | −3.36 | 7.51 | −20.43 |
| 2.4E−4 | 13.01 | 24.53 | 24.53 | −3.62 | 7.39 | 2.87 |
| 6.1E−05 | 4.25 | 9.32 | 9.32 | 2.85 | 13.07 | −1.53 |

In Tables 5, 6 and 7 above, the two columns of values for each bispecific antibody were the results of two duplicate experiments.

Although the present disclosure has been specified with general descriptions and specific embodiments above, it is apparent to those skilled in the art that some modifications or improvements can be made based on the present disclosure. Therefore, any modifications or improvements without departing from the spirit of the present disclosure are within the scope of the present disclosure.

INDUSTRIAL APPLICABILITY

The present disclosure relates to a bispecific antibody binding to BCMA and CD3 and a preparation method therefore and the use thereof. The present disclosure provides a bispecific antibody, which can simultaneously bind to BCMA and CD3, has a specific targeting effect and can efficiently stimulate directed immune responses. The bispecific antibody retains the biological functions of an anti-CD3 antibody and an anti-BCMA antibody, enables the bispecific antibody molecule to achieve excellent biological functions of simultaneously binding to BCMA and CD3 in a targeted manner, forms a bridge between tumor cells and immune effector cells, effectively activates the immune effect or cells and the directed immune response, significantly enhances the effects of immune cells in killing tumor cells, has a high targeted cell killing efficiency, and reduces the ADCC effect to the largest extent, has high safety, and has good application prospects in tumor immunotherapy.

What is claimed is:

1. A bispecific antibody binding to BCMA and CD3, comprising:

a first domain, binding to B cell maturation antigen BCMA, and a second domain, binding to T cell surface antigen CD3, wherein the first domain and the second domain are connected by linker peptides, wherein the first domain comprises a heavy chain variable region and a light chain variable region, and the heavy chain variable region and the light chain variable region of the first domain comprise amino acid sequences selected from the grouping consisting of:

(1) the heavy chain variable region of the first domain has the amino acid sequence represented by SEQ ID NO.17, and the light chain variable region of the first domain has the amino acid sequence represented by SEQ ID NO.18;

(2) the heavy chain variable region of the first domain has the amino acid sequence represented by SEQ ID NO.20, and the light chain variable region of the first domain has the amino acid sequence represented by SEQ ID NO.22;

(3) the heavy chain variable region of the first domain has the amino acid sequence represented by SEQ ID NO.19, and the light chain variable region of the first domain has the amino acid sequence represented by SEQ ID NO.27;

(4) the heavy chain variable region of the first domain has the amino acid sequence represented by SEQ ID NO.21, and the light chain variable region of the first domain has the amino acid sequence represented by SEQ ID NO.25; and (5) the heavy chain variable region of the first domain has the amino acid sequence represented by SEQ ID NO.20, and the light chain variable region of the first domain has the amino acid sequence represented by SEQ ID NO.26;

and wherein the second domain comprises a heavy chain variable region comprising the amino acid sequence represented by SEQ ID NO.28, and a light chain variable region comprising the amino acid sequence represented by SEQ ID NO.29.

2. The bispecific antibody binding to BCMA and CD3 of claim 1, wherein the first domain comprises a heavy chain and a light chain, wherein the first domain consists of two complete light chain-heavy chain pairs connected by disulfide bonds, and wherein the heavy chain comprises an Fc fragment of a human or humanized antibody selected from the group consisting of IgG1, IgG2, IgA, IgE, IgM, IgG4 and IgD.

3. The bispecific antibody binding to BCMA and CD3 of claim 1, wherein the first domain comprises a heavy chain and a light chain, wherein the heavy chain and the light chain comprise amino acid sequences selected from the group consisting of:

(1) the heavy chain of the first domain comprising the amino acid sequence represented by SEQ ID NO.32, and the light chain of the first domain comprising the amino acid sequence represented by SEQ ID NO.33, (2) the heavy chain of the first domain comprising the amino acid sequence represented by SEQ ID NO.49, and the light chain of the first domain comprising the amino acid sequence represented by SEQ ID NO.42, (3) the heavy chain of the first domain comprising the amino acid sequence represented by SEQ ID NO.50, and the light chain of the first domain comprising the amino acid sequence represented by SEQ ID NO.44, (4) the heavy chain of the first domain comprising the amino acid sequence represented by SEQ ID NO.51, and the light chain of the first domain comprising the amino acid sequence represented by SEQ ID NO.46, and (5) the heavy chain of the first domain comprising the amino acid sequence represented by SEQ ID NO.52, and the light chain of the first domain comprising the amino acid sequence represented by SEQ ID NO.48.

4. The bispecific antibody binding to BCMA and CD3 of claim 1, wherein the light chain variable region and the heavy chain variable region of the second domain are connected by linker peptides, to form a single-chain antibody, comprising the amino acid sequence represented by SEQ ID NO.31.

5. The bispecific antibody binding to BCMA and CD3 of claim 1, wherein the second domain contains two single-chain antibodies, which are connected in any of the following manners to form symmetrical structure:

(1) the C-termini of the two single-chain antibodies of the second domain are respectively connected to the N-termini of the two heavy chains of the first domain through linker peptides; or (2) the N-termini of the two single-chain antibodies of the second domain are respectively connected to the C-termini of the two heavy chains of the first domain through linker peptides;

wherein the amino acid sequence of the linker peptide is represented by SEQ ID NO.30.

6. The bispecific antibody binding to BCMA and CD3 of claim 1, wherein the heavy chain variable region of the first domain is connected with the second domain to form a linker peptide, wherein the linker peptide and the light chain variable region of the first domain comprise amino acid sequences selected from the group consisting of:

(1) the linker peptide comprising an amino acid sequence represented by SEQ ID NO.34 or 35, and the light chain of the first domain comprising the amino acid sequence represented by SEQ ID NO.33;

(2) the a linker peptide comprising an amino acid sequence represented by SEQ ID NO.41, and the light chain of the first domain comprising the amino acid sequence represented by SEQ ID NO.42;

(3) the linker peptide comprising an amino acid sequence represented by SEQ ID NO.43, and the light chain of the first domain comprising the amino acid sequence represented by SEQ ID NO.44;

(4) the linker peptide comprising an amino acid sequence represented by SEQ ID NO.45, and the light chain of the first domain comprising the amino acid sequence represented by SEQ ID NO.46; and (5) the a linker peptide comprising an amino acid sequence represented by SEQ ID NO.47, and the light chain of the first domain comprising the amino acid sequence represented by SEQ ID NO.48.

7. A nucleic acid encoding the bispecific antibody binding to BCMA and CD3 of claim 1.

8. A biological material containing the nucleic acid of claim 7, the biological material consists of recombinant DNA, expression cassette, vector, host cell, engineering bacteria or cell line.

9. A method for preparing the bispecific antibody binding to BCMA and CD3 of claim 1, wherein the method consists of: constructing expression vector containing coding genes of the first domain and the second domain; introducing the expression vector into host cells, obtaining host cells expressing the bispecific antibody; culturing the host cells, and obtaining a bispecific antibody through separation and purification.

10. A multispecific antibody fusion proteins, immunotoxins, medicines or detection reagents comprising the bispecific antibody binding to BCMA and CD3 of claim 1.

* * * * *

SEQUENCE LISTING

<160> NUMBER OF SEQ ID NOS: 52

<210> SEQ ID NO 1
<211> LENGTH: 13
<212> TYPE: PRT
<213> ORGANISM: Artificial Sequence
<220> FEATURE:
<223> OTHER INFORMATION: Laboratory synthesis

<400> SEQUENCE: 1

```
Ser Gly Ser Ser Ser Asn Ile Gly Gly Tyr Ser Val Asn
1               5                   10
```

<210> SEQ ID NO 2
<211> LENGTH: 7
<212> TYPE: PRT
<213> ORGANISM: Artificial Sequence
<220> FEATURE:
<223> OTHER INFORMATION: Laboratory synthesis

<400> SEQUENCE: 2

```
Arg Asn Asn Gln Arg Pro Ser
1               5
```

<210> SEQ ID NO 3
<211> LENGTH: 11
<212> TYPE: PRT
<213> ORGANISM: Artificial Sequence
<220> FEATURE:
<223> OTHER INFORMATION: Laboratory synthesis

<400> SEQUENCE: 3

```
Ala Ala Trp Asp Asp Ser Leu Ile Gly Tyr Val
1               5                   10
```

<210> SEQ ID NO 4
<211> LENGTH: 5
<212> TYPE: PRT
<213> ORGANISM: Artificial Sequence
<220> FEATURE:
<223> OTHER INFORMATION: Laboratory synthesis

<400> SEQUENCE: 4

```
Ser Tyr Ala Ile Ser
1               5
```

<210> SEQ ID NO 5
<211> LENGTH: 17
<212> TYPE: PRT
<213> ORGANISM: Artificial Sequence
<220> FEATURE:
<223> OTHER INFORMATION: Laboratory synthesis

<400> SEQUENCE: 5

```
Gly Ile Ile Pro Ile Phe Gly Thr Ala Asn Tyr Ala Gln Lys Phe Gln
1               5                   10                  15

Gly
```

<210> SEQ ID NO 6
<211> LENGTH: 6
<212> TYPE: PRT
<213> ORGANISM: Artificial Sequence
<220> FEATURE:
<223> OTHER INFORMATION: Laboratory synthesis

<400> SEQUENCE: 6

Gly Trp Tyr Phe Asp Leu
1 5

<210> SEQ ID NO 7
<211> LENGTH: 5
<212> TYPE: PRT
<213> ORGANISM: Artificial Sequence
<220> FEATURE:
<223> OTHER INFORMATION: Laboratory synthesis

<400> SEQUENCE: 7

Lys Ser Ala Ile Met
1 5

<210> SEQ ID NO 8
<211> LENGTH: 5
<212> TYPE: PRT
<213> ORGANISM: Artificial Sequence
<220> FEATURE:
<223> OTHER INFORMATION: Laboratory synthesis

<400> SEQUENCE: 8

Lys Ser Ala Ile Gln
1 5

<210> SEQ ID NO 9
<211> LENGTH: 5
<212> TYPE: PRT
<213> ORGANISM: Artificial Sequence
<220> FEATURE:
<223> OTHER INFORMATION: Laboratory synthesis

<400> SEQUENCE: 9

Lys Ser Ala Ile His
1 5

<210> SEQ ID NO 10
<211> LENGTH: 17
<212> TYPE: PRT
<213> ORGANISM: Artificial Sequence
<220> FEATURE:
<223> OTHER INFORMATION: Laboratory synthesis

<400> SEQUENCE: 10

Gly Val Ile Pro Ile Phe Gly Thr Ala Asn Tyr Ala Gln Lys Phe Gln
1 5 10 15

Gly

<210> SEQ ID NO 11
<211> LENGTH: 6
<212> TYPE: PRT
<213> ORGANISM: Artificial Sequence
<220> FEATURE:
<223> OTHER INFORMATION: Laboratory synthesis

<400> SEQUENCE: 11

Gly Trp Tyr Leu Asp Leu
1 5

<210> SEQ ID NO 12
<211> LENGTH: 13
<212> TYPE: PRT
<213> ORGANISM: Artificial Sequence
<220> FEATURE:
<223> OTHER INFORMATION: Laboratory synthesis

<400> SEQUENCE: 12

Ser Gly Ser Ser Asn Asn Ile Gly Gly Tyr Ser Val Asn
1 5 10

<210> SEQ ID NO 13
<211> LENGTH: 11
<212> TYPE: PRT
<213> ORGANISM: Artificial Sequence
<220> FEATURE:
<223> OTHER INFORMATION: Laboratory synthesis

<400> SEQUENCE: 13

Ala Ala Trp Asp Asp Ser Val Ile Gly Trp Leu
1 5 10

<210> SEQ ID NO 14
<211> LENGTH: 11
<212> TYPE: PRT
<213> ORGANISM: Artificial Sequence
<220> FEATURE:
<223> OTHER INFORMATION: Laboratory synthesis

<400> SEQUENCE: 14

Ala Ala Trp Asp Asp Ser Val Ile Gly Leu Leu
1 5 10

<210> SEQ ID NO 15
<211> LENGTH: 11
<212> TYPE: PRT
<213> ORGANISM: Artificial Sequence
<220> FEATURE:
<223> OTHER INFORMATION: Laboratory synthesis

<400> SEQUENCE: 15

Ala Ala Trp Asp Asp Ser Val Ile Gly Trp Val
1 5 10

<210> SEQ ID NO 16
<211> LENGTH: 11
<212> TYPE: PRT
<213> ORGANISM: Artificial Sequence
<220> FEATURE:
<223> OTHER INFORMATION: Laboratory synthesis

<400> SEQUENCE: 16

Ala Ala Trp Asp Asp Ser Glu Ile Gly Trp Leu
1 5 10

<210> SEQ ID NO 17
<211> LENGTH: 115
<212> TYPE: PRT
<213> ORGANISM: Artificial Sequence
<220> FEATURE:
<223> OTHER INFORMATION: Laboratory synthesis

<400> SEQUENCE: 17

Gln Val Gln Leu Gln Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Glu Ser Thr Ser Thr Ala Tyr

```
65                  70                  75                  80

Met Glu Leu Ser Ser Leu Arg Ser Glu Asp Thr Ala Val Tyr Tyr Cys
                85                  90                  95

Ala Arg Gly Trp Tyr Phe Asp Leu Trp Gly Arg Gly Thr Leu Val Thr
            100                 105                 110

Val Ser Ser
        115


<210> SEQ ID NO 18
<211> LENGTH: 110
<212> TYPE: PRT
<213> ORGANISM: Artificial Sequence
<220> FEATURE:
<223> OTHER INFORMATION: Laboratory synthesis

<400> SEQUENCE: 18

Leu Pro Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Gly Tyr
            20                  25                  30

Ser Val Asn Trp Tyr Gln Gln Phe Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Ala Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Ile Gly Tyr Val Phe Gly Thr Gly Thr Gln Leu Thr Val Leu
            100                 105                 110


<210> SEQ ID NO 19
<211> LENGTH: 115
<212> TYPE: PRT
<213> ORGANISM: Artificial Sequence
<220> FEATURE:
<223> OTHER INFORMATION: Laboratory synthesis

<400> SEQUENCE: 19

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Lys Ser
            20                  25                  30

Ala Ile Met Trp Val Arg Gln Ala Pro Gly Gln Gly Leu Glu Trp Met
        35                  40                  45

Gly Gly Val Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Trp Tyr Leu Asp Leu Trp Gly Arg Gly Thr Leu Val Thr
            100                 105                 110

Val Ser Ser
        115


<210> SEQ ID NO 20
<211> LENGTH: 115
```

<212> TYPE: PRT
<213> ORGANISM: Artificial Sequence
<220> FEATURE:
<223> OTHER INFORMATION: Laboratory synthesis

<400> SEQUENCE: 20

```
Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Lys Ser
            20                  25                  30

Ala Ile Gln Trp Val Arg Gln Ala Pro Gly Gln Gly Leu Glu Trp Met
        35                  40                  45

Gly Gly Val Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Trp Tyr Leu Asp Leu Trp Gly Arg Gly Thr Leu Val Thr
            100                 105                 110

Val Ser Ser
        115
```

<210> SEQ ID NO 21
<211> LENGTH: 115
<212> TYPE: PRT
<213> ORGANISM: Artificial Sequence
<220> FEATURE:
<223> OTHER INFORMATION: Laboratory synthesis

<400> SEQUENCE: 21

```
Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Lys Ser
            20                  25                  30

Ala Ile His Trp Val Arg Gln Ala Pro Gly Gln Gly Leu Glu Trp Met
        35                  40                  45

Gly Gly Val Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Trp Tyr Leu Asp Leu Trp Gly Arg Gly Thr Leu Val Thr
            100                 105                 110

Val Ser Ser
        115
```

<210> SEQ ID NO 22
<211> LENGTH: 110
<212> TYPE: PRT
<213> ORGANISM: Artificial Sequence
<220> FEATURE:
<223> OTHER INFORMATION: Laboratory synthesis

<400> SEQUENCE: 22

```
Leu Pro Val Leu Thr Gln Pro Pro Ser Ala Ser Gly Thr Pro Gly Gln
1               5                   10                  15

Arg Val Thr Ile Ser Cys Ser Gly Ser Ser Asn Asn Ile Gly Gly Tyr
```

```
            20                  25                  30

Ser Val Asn Trp Tyr Gln Gln Phe Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Ala Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Val
                85                  90                  95

Ile Gly Trp Leu Phe Gly Thr Gly Thr Gln Leu Thr Val Leu
            100                 105                 110


<210> SEQ ID NO 23
<211> LENGTH: 110
<212> TYPE: PRT
<213> ORGANISM: Artificial Sequence
<220> FEATURE:
<223> OTHER INFORMATION: Laboratory synthesis

<400> SEQUENCE: 23

Leu Pro Val Leu Thr Gln Pro Pro Ser Ala Ser Gly Thr Pro Gly Gln
1               5                   10                  15

Arg Val Thr Ile Ser Cys Ser Gly Ser Ser Asn Asn Ile Gly Gly Tyr
            20                  25                  30

Ser Val Asn Trp Tyr Gln Gln Phe Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Ala Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Val
                85                  90                  95

Ile Gly Leu Leu Phe Gly Thr Gly Thr Gln Leu Thr Val Leu
            100                 105                 110


<210> SEQ ID NO 24
<211> LENGTH: 110
<212> TYPE: PRT
<213> ORGANISM: Artificial Sequence
<220> FEATURE:
<223> OTHER INFORMATION: Laboratory synthesis

<400> SEQUENCE: 24

Leu Pro Val Leu Thr Gln Pro Pro Ser Ala Ser Gly Thr Pro Gly Gln
1               5                   10                  15

Arg Val Thr Ile Ser Cys Ser Gly Ser Ser Asn Asn Ile Gly Gly Tyr
            20                  25                  30

Ser Val Asn Trp Tyr Gln Gln Phe Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Ala Ser Phe Ser Leu Ala Ile Ser Gly Leu Gln
65                  70                  75                  80

Phe Glu Asp Glu Ala Asp Tyr Tyr Cys Ala Ala Trp Asp Asp Ser Val
                85                  90                  95

Ile Gly Trp Val Leu Gly Thr Gly Thr Gln Leu Thr Val Leu
            100                 105                 110
```

<210> SEQ ID NO 25
<211> LENGTH: 110
<212> TYPE: PRT
<213> ORGANISM: Artificial Sequence
<220> FEATURE:
<223> OTHER INFORMATION: Laboratory synthesis

<400> SEQUENCE: 25

Leu Pro Val Leu Thr Gln Pro Pro Ser Ala Ser Gly Thr Pro Gly Gln
1 5 10 15

Arg Val Thr Ile Ser Cys Ser Gly Ser Ser Ser Asn Ile Gly Gly Tyr
20 25 30

Ser Val Asn Trp Tyr Gln Gln Phe Pro Gly Thr Ala Pro Lys Leu Leu
35 40 45

Ile Tyr Arg Asn Asn Gln Arg Pro Ser Gly Val Pro Asp Arg Phe Ser
50 55 60

Gly Ser Lys Ser Gly Ala Ser Ala Ser Leu Ala Ile Ser Gly Leu Gln
65 70 75 80

Ser Glu Asp Val Ala Asp Tyr Tyr Cys Ala Ala Trp Asp Asp Ser Leu
85 90 95

Ile Gly Tyr Val Phe Gly Thr Gly Thr Gln Leu Thr Val Leu
100 105 110

<210> SEQ ID NO 26
<211> LENGTH: 110
<212> TYPE: PRT
<213> ORGANISM: Artificial Sequence
<220> FEATURE:
<223> OTHER INFORMATION: Laboratory synthesis

<400> SEQUENCE: 26

Leu Pro Val Leu Thr Gln Pro Pro Ser Ala Ser Gly Thr Pro Gly Gln
1 5 10 15

Arg Val Thr Ile Ser Cys Ser Gly Ser Ser Asn Asn Ile Gly Gly Tyr
20 25 30

Ser Val Asn Trp Tyr Gln Gln Phe Pro Gly Thr Ala Pro Lys Leu Leu
35 40 45

Ile Tyr Arg Asn Asn Gln Arg Pro Ser Gly Val Pro Asp Arg Phe Ser
50 55 60

Gly Ser Lys Ser Gly Ala Ser Ala Ser Leu Ala Ile Ser Gly Leu Gln
65 70 75 80

Ser Glu Asp Glu Ala Asp Tyr Tyr Cys Ala Ala Trp Asp Asp Ser Glu
85 90 95

Ile Gly Trp Leu Phe Gly Thr Gly Thr Gln Leu Thr Val Leu
100 105 110

<210> SEQ ID NO 27
<211> LENGTH: 110
<212> TYPE: PRT
<213> ORGANISM: Artificial Sequence
<220> FEATURE:
<223> OTHER INFORMATION: Laboratory synthesis

<400> SEQUENCE: 27

Leu Pro Val Leu Thr Gln Pro Pro Ser Ala Ser Gly Thr Pro Gly Gln
1 5 10 15

Arg Val Thr Ile Ser Cys Ser Gly Ser Ser Asn Asn Ile Gly Gly Tyr
20 25 30

Ser Val Asn Trp Tyr Gln Gln Phe Pro Gly Thr Ala Pro Lys Leu Leu

```
        35                  40                  45

Ile Tyr Arg Asn Asn Gln Arg Pro Ser Gly Val Pro Asp Arg Phe Ser
    50                  55                  60

Gly Ser Lys Ser Gly Ala Ser Phe Ser Leu Ala Ile Ser Gly Leu Gln
65                  70                  75                  80

Phe Glu Asp Glu Ala Asp Tyr Tyr Cys Ala Arg Trp Asp Asp Ser Val
                85                  90                  95

Ile Gly Trp Val Leu Gly Thr Gly Thr Gln Leu Thr Val Leu
            100                 105                 110


<210> SEQ ID NO 28
<211> LENGTH: 122
<212> TYPE: PRT
<213> ORGANISM: Artificial Sequence
<220> FEATURE:
<223> OTHER INFORMATION: Laboratory synthesis

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Thr Met Asn Trp Val Arg Gln Ala Pro Gly Lys Cys Leu Glu Trp Val
        35                  40                  45

Ala Leu Ile Asn Pro Tyr Lys Gly Val Thr Thr Tyr Ala Asp Ser Val
    50                  55                  60

Lys Gly Arg Phe Thr Ile Ser Val Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Tyr Gly Asp Ser Asp Trp Tyr Phe Asp Val Trp
            100                 105                 110

Gly Gln Gly Thr Leu Val Thr Val Ser Ser
        115                 120


<210> SEQ ID NO 29
<211> LENGTH: 107
<212> TYPE: PRT
<213> ORGANISM: Artificial Sequence
<220> FEATURE:
<223> OTHER INFORMATION: Laboratory synthesis

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Cys Gly Thr Lys Val Glu Ile Lys
            100                 105
```

<210> SEQ ID NO 30
<211> LENGTH: 10
<212> TYPE: PRT
<213> ORGANISM: Artificial Sequence
<220> FEATURE:
<223> OTHER INFORMATION: Laboratory synthesis

<400> SEQUENCE: 30

```
Gly Gly Gly Gly Ser Gly Gly Gly Gly Ser
1               5                   10
```

<210> SEQ ID NO 31
<211> LENGTH: 244
<212> TYPE: PRT
<213> ORGANISM: Artificial Sequence
<220> FEATURE:
<223> OTHER INFORMATION: Laboratory synthesis

<400> SEQUENCE: 31

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
            85                  90                  95

Thr Phe Gly Cys Gly Thr Lys Val Glu Ile Lys Gly Gly Gly Gly Ser
            100                 105                 110

Gly Gly Gly Gly Ser Gly Gly Gly Gly Ser Glu Val Gln Leu Val Glu
        115                 120                 125

Ser Gly Gly Gly Leu Val Gln Pro Gly Gly Ser Leu Arg Leu Ser Cys
    130                 135                 140

Ala Ala Ser Gly Tyr Ser Phe Thr Gly Tyr Thr Met Asn Trp Val Arg
145                 150                 155                 160

Gln Ala Pro Gly Lys Cys Leu Glu Trp Val Ala Leu Ile Asn Pro Tyr
                165                 170                 175

Lys Gly Val Thr Thr Tyr Ala Asp Ser Val Lys Gly Arg Phe Thr Ile
            180                 185                 190

Ser Val Asp Lys Ser Lys Asn Thr Ala Tyr Leu Gln Met Asn Ser Leu
        195                 200                 205

Arg Ala Glu Asp Thr Ala Val Tyr Tyr Cys Ala Arg Ser Gly Tyr Tyr
    210                 215                 220

Gly Asp Ser Asp Trp Tyr Phe Asp Val Trp Gly Gln Gly Thr Leu Val
225                 230                 235                 240

Thr Val Ser Ser
```

<210> SEQ ID NO 32
<211> LENGTH: 442
<212> TYPE: PRT
<213> ORGANISM: Artificial Sequence
<220> FEATURE:
<223> OTHER INFORMATION: Laboratory synthesis

<400> SEQUENCE: 32

```
Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Lys Ser
            20                  25                  30

Ala Ile Gln Trp Val Arg Gln Ala Pro Gly Gln Gly Leu Glu Trp Met
        35                  40                  45

Gly Gly Val Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Trp Tyr Leu Asp Leu Trp Gly Arg Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly Pro Pro Cys Pro Pro Cys
    210                 215                 220

Pro Ala Pro Glu Phe Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415
```

```
Val Phe Ser Cys Ser Val Met His Glu Ala Leu His Asn His Tyr Thr
            420                 425                 430

Gln Lys Ser Leu Ser Leu Ser Leu Gly Lys
        435                 440


<210> SEQ ID NO 33
<211> LENGTH: 216
<212> TYPE: PRT
<213> ORGANISM: Artificial Sequence
<220> FEATURE:
<223> OTHER INFORMATION: Laboratory synthesis

<400> SEQUENCE: 33

Leu Pro Val Leu Thr Gln Pro Pro Ser Ala Ser Gly Thr Pro Gly Gln
1               5                   10                  15

Arg Val Thr Ile Ser Cys Ser Gly Ser Ser Asn Asn Ile Gly Gly Tyr
            20                  25                  30

Ser Val Asn Trp Tyr Gln Gln Phe Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Ala Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Val
                85                  90                  95

Ile Gly Trp Leu Phe Gly Thr Gly Thr Gln Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215


<210> SEQ ID NO 34
<211> LENGTH: 696
<212> TYPE: PRT
<213> ORGANISM: Artificial Sequence
<220> FEATURE:
<223> OTHER INFORMATION: Laboratory synthesis

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
    50                  55                  60
```

```
Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Cys Gly Thr Lys Val Glu Ile Lys Gly Gly Gly Gly Ser
            100                 105                 110

Gly Gly Gly Gly Ser Gly Gly Gly Gly Ser Glu Val Gln Leu Val Glu
        115                 120                 125

Ser Gly Gly Gly Leu Val Gln Pro Gly Gly Ser Leu Arg Leu Ser Cys
    130                 135                 140

Ala Ala Ser Gly Tyr Ser Phe Thr Gly Tyr Thr Met Asn Trp Val Arg
145                 150                 155                 160

Gln Ala Pro Gly Lys Cys Leu Glu Trp Val Ala Leu Ile Asn Pro Tyr
                165                 170                 175

Lys Gly Val Thr Thr Tyr Ala Asp Ser Val Lys Gly Arg Phe Thr Ile
            180                 185                 190

Ser Val Asp Lys Ser Lys Asn Thr Ala Tyr Leu Gln Met Asn Ser Leu
        195                 200                 205

Arg Ala Glu Asp Thr Ala Val Tyr Tyr Cys Ala Arg Ser Gly Tyr Tyr
    210                 215                 220

Gly Asp Ser Asp Trp Tyr Phe Asp Val Trp Gly Gln Gly Thr Leu Val
225                 230                 235                 240

Thr Val Ser Ser Gly Gly Gly Gly Ser Gly Gly Gly Gly Ser Gln Val
                245                 250                 255

Gln Leu Gln Gln Ser Gly Ala Glu Val Lys Lys Pro Gly Ser Ser Val
            260                 265                 270

Lys Val Ser Cys Lys Ala Ser Gly Gly Thr Phe Ser Ser Tyr Ala Ile
        275                 280                 285

Ser Trp Val Arg Gln Ala Pro Gly Gln Gly Leu Glu Trp Met Gly Gly
    290                 295                 300

Ile Ile Pro Ile Phe Gly Thr Ala Asn Tyr Ala Gln Lys Phe Gln Gly
305                 310                 315                 320

Arg Val Thr Ile Thr Ala Asp Glu Ser Thr Ser Thr Ala Tyr Met Glu
                325                 330                 335

Leu Ser Ser Leu Arg Ser Glu Asp Thr Ala Val Tyr Tyr Cys Ala Arg
            340                 345                 350

Gly Trp Tyr Phe Asp Leu Trp Gly Arg Gly Thr Leu Val Thr Val Ser
        355                 360                 365

Ser Ala Ser Thr Lys Gly Pro Ser Val Phe Pro Leu Ala Pro Cys Ser
    370                 375                 380

Arg Ser Thr Ser Glu Ser Thr Ala Ala Leu Gly Cys Leu Val Lys Asp
385                 390                 395                 400

Tyr Phe Pro Glu Pro Val Thr Val Ser Trp Asn Ser Gly Ala Leu Thr
                405                 410                 415

Ser Gly Val His Thr Phe Pro Ala Val Leu Gln Ser Ser Gly Leu Tyr
            420                 425                 430

Ser Leu Ser Ser Val Val Thr Val Pro Ser Ser Ser Leu Gly Thr Lys
        435                 440                 445

Thr Tyr Thr Cys Asn Val Asp His Lys Pro Ser Asn Thr Lys Val Asp
    450                 455                 460

Lys Arg Val Glu Ser Lys Tyr Gly Pro Pro Cys Pro Pro Cys Pro Ala
465                 470                 475                 480
```

```
Pro Glu Phe Leu Gly Gly Pro Ser Val Phe Leu Phe Pro Pro Lys Pro
                485                 490                 495

Lys Asp Thr Leu Met Ile Ser Arg Thr Pro Glu Val Thr Cys Val Val
            500                 505                 510

Val Asp Val Ser Gln Glu Asp Pro Glu Val Gln Phe Asn Trp Tyr Val
        515                 520                 525

Asp Gly Val Glu Val His Asn Ala Lys Thr Lys Pro Arg Glu Glu Gln
    530                 535                 540

Phe Asn Ser Thr Tyr Arg Val Val Ser Val Leu Thr Val Leu His Gln
545                 550                 555                 560

Asp Trp Leu Asn Gly Lys Glu Tyr Lys Cys Lys Val Ser Asn Lys Gly
                565                 570                 575

Leu Pro Ser Ser Ile Glu Lys Thr Ile Ser Lys Ala Lys Gly Gln Pro
            580                 585                 590

Arg Glu Pro Gln Val Tyr Thr Leu Pro Pro Ser Gln Glu Glu Met Thr
        595                 600                 605

Lys Asn Gln Val Ser Leu Thr Cys Leu Val Lys Gly Phe Tyr Pro Ser
    610                 615                 620

Asp Ile Ala Val Glu Trp Glu Ser Asn Gly Gln Pro Glu Asn Asn Tyr
625                 630                 635                 640

Lys Thr Thr Pro Pro Val Leu Asp Ser Asp Gly Ser Phe Phe Leu Tyr
                645                 650                 655

Ser Arg Leu Thr Val Asp Lys Ser Arg Trp Gln Glu Gly Asn Val Phe
            660                 665                 670

Ser Cys Ser Val Met His Glu Ala Leu His Asn His Tyr Thr Gln Lys
        675                 680                 685

Ser Leu Ser Leu Ser Leu Gly Lys
    690                 695


<210> SEQ ID NO 35
<211> LENGTH: 696
<212> TYPE: PRT
<213> ORGANISM: Artificial Sequence
<220> FEATURE:
<223> OTHER INFORMATION: Laboratory synthesis

<400> SEQUENCE: 35

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Lys Ser
            20                  25                  30

Ala Ile Gln Trp Val Arg Gln Ala Pro Gly Gln Gly Leu Glu Trp Met
        35                  40                  45

Gly Gly Val Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Trp Tyr Leu Asp Leu Trp Gly Arg Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140
```

-continued

```
Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly Pro Pro Cys Pro Pro Cys
    210                 215                 220

Pro Ala Pro Glu Phe Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Lys Ser Leu Ser Leu Ser Leu Gly Lys Gly Gly Gly Gly Ser Gly
        435                 440                 445

Gly Gly Gly Ser Asp Ile Gln Met Thr Gln Ser Pro Ser Ser Leu Ser
    450                 455                 460

Ala Ser Val Gly Asp Arg Val Thr Ile Thr Cys Arg Ala Ser Gln Asp
465                 470                 475                 480

Ile Arg Asn Tyr Leu Asn Trp Tyr Gln Gln Lys Pro Gly Lys Ala Pro
                485                 490                 495

Lys Leu Leu Ile Tyr Tyr Thr Ser Arg Leu Glu Ser Gly Val Pro Ser
            500                 505                 510

Arg Phe Ser Gly Ser Gly Ser Gly Thr Asp Tyr Thr Leu Thr Ile Ser
        515                 520                 525

Ser Leu Gln Pro Glu Asp Phe Ala Thr Tyr Tyr Cys Gln Gln Gly Asn
    530                 535                 540

Thr Leu Pro Trp Thr Phe Gly Cys Gly Thr Lys Val Glu Ile Lys Gly
545                 550                 555                 560

Gly Gly Gly Ser Gly Gly Gly Gly Ser Gly Gly Gly Gly Ser Glu Val
```

```
                565                 570                 575

Gln Leu Val Glu Ser Gly Gly Gly Leu Val Gln Pro Gly Gly Ser Leu
            580                 585                 590

Arg Leu Ser Cys Ala Ala Ser Gly Tyr Ser Phe Thr Gly Tyr Thr Met
        595                 600                 605

Asn Trp Val Arg Gln Ala Pro Gly Lys Cys Leu Glu Trp Val Ala Leu
    610                 615                 620

Ile Asn Pro Tyr Lys Gly Val Thr Thr Tyr Ala Asp Ser Val Lys Gly
625                 630                 635                 640

Arg Phe Thr Ile Ser Val Asp Lys Ser Lys Asn Thr Ala Tyr Leu Gln
                645                 650                 655

Met Asn Ser Leu Arg Ala Glu Asp Thr Ala Val Tyr Tyr Cys Ala Arg
            660                 665                 670

Ser Gly Tyr Tyr Gly Asp Ser Asp Trp Tyr Phe Asp Val Trp Gly Gln
        675                 680                 685

Gly Thr Leu Val Thr Val Ser Ser
    690                 695


<210> SEQ ID NO 36
<211> LENGTH: 246
<212> TYPE: PRT
<213> ORGANISM: Artificial Sequence
<220> FEATURE:
<223> OTHER INFORMATION: Laboratory synthesis

<400> SEQUENCE: 36

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Trp Tyr Phe Asp Leu Trp Gly Arg Gly Thr Leu Val Thr
            100                 105                 110

Val Ser Ser Ala Ser Thr Gly Gly Ser Ser Arg Ser Ser Ser Ser Gly
        115                 120                 125

Gly Gly Gly Ser Gly Gly Gly Gly Leu Pro Val Leu Thr Gln Pro Pro
    130                 135                 140

Ser Ala Ser Gly Thr Pro Gly Gln Arg Val Thr Ile Ser Cys Ser Gly
145                 150                 155                 160

Ser Ser Ser Asn Ile Gly Gly Tyr Ser Val Asn Trp Tyr Gln Gln Phe
                165                 170                 175

Pro Gly Thr Ala Pro Lys Leu Leu Ile Tyr Arg Asn Asn Gln Arg Pro
            180                 185                 190

Ser Gly Val Pro Asp Arg Phe Ser Gly Ser Lys Ser Gly Ala Ser Ala
        195                 200                 205

Ser Leu Ala Ile Ser Gly Leu Gln Ser Glu Asp Glu Ala Asp Tyr Tyr
    210                 215                 220

Cys Ala Ala Trp Asp Asp Ser Leu Ile Gly Tyr Val Phe Gly Thr Gly
```

```
225                 230                 235                 240

Thr Gln Leu Thr Val Leu
                245


<210> SEQ ID NO 37
<211> LENGTH: 246
<212> TYPE: PRT
<213> ORGANISM: Artificial Sequence
<220> FEATURE:
<223> OTHER INFORMATION: Laboratory synthesis

<400> SEQUENCE: 37

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Lys Ser
            20                  25                  30

Ala Ile Gln Trp Val Arg Gln Ala Pro Gly Gln Gly Leu Glu Trp Met
        35                  40                  45

Gly Gly Val Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Trp Tyr Leu Asp Leu Trp Gly Arg Gly Thr Leu Val Thr
            100                 105                 110

Val Ser Ser Ala Ser Thr Gly Gly Ser Ser Arg Ser Ser Ser Ser Gly
        115                 120                 125

Gly Gly Gly Ser Gly Gly Gly Gly Leu Pro Val Leu Thr Gln Pro Pro
    130                 135                 140

Ser Ala Ser Gly Thr Pro Gly Gln Arg Val Thr Ile Ser Cys Ser Gly
145                 150                 155                 160

Ser Ser Asn Asn Ile Gly Gly Tyr Ser Val Asn Trp Tyr Gln Gln Phe
                165                 170                 175

Pro Gly Thr Ala Pro Lys Leu Leu Ile Tyr Arg Asn Asn Gln Arg Pro
            180                 185                 190

Ser Gly Val Pro Asp Arg Phe Ser Gly Ser Lys Ser Gly Ala Ser Ala
        195                 200                 205

Ser Leu Ala Ile Ser Gly Leu Gln Ser Glu Asp Glu Ala Asp Tyr Tyr
    210                 215                 220

Cys Ala Ala Trp Asp Asp Ser Val Ile Gly Trp Leu Phe Gly Thr Gly
225                 230                 235                 240

Thr Gln Leu Thr Val Leu
                245


<210> SEQ ID NO 38
<211> LENGTH: 246
<212> TYPE: PRT
<213> ORGANISM: Artificial Sequence
<220> FEATURE:
<223> OTHER INFORMATION: Laboratory synthesis

<400> SEQUENCE: 38

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Lys Ser
            20                  25                  30
```

```
Ala Ile Met Trp Val Arg Gln Ala Pro Gly Gln Gly Leu Glu Trp Met
        35                  40                  45

Gly Gly Val Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Trp Tyr Leu Asp Leu Trp Gly Arg Gly Thr Leu Val Thr
            100                 105                 110

Val Ser Ser Ala Ser Thr Gly Gly Ser Ser Arg Ser Ser Ser Ser Gly
        115                 120                 125

Gly Gly Gly Ser Gly Gly Gly Gly Leu Pro Val Leu Thr Gln Pro Pro
    130                 135                 140

Ser Ala Ser Gly Thr Pro Gly Gln Arg Val Thr Ile Ser Cys Ser Gly
145                 150                 155                 160

Ser Ser Asn Asn Ile Gly Gly Tyr Ser Val Asn Trp Tyr Gln Gln Phe
                165                 170                 175

Pro Gly Thr Ala Pro Lys Leu Leu Ile Tyr Arg Asn Asn Gln Arg Pro
            180                 185                 190

Ser Gly Val Pro Asp Arg Phe Ser Gly Ser Lys Ser Gly Ala Ser Phe
        195                 200                 205

Ser Leu Ala Ile Ser Gly Leu Gln Phe Glu Asp Glu Ala Asp Tyr Tyr
    210                 215                 220

Cys Ala Arg Trp Asp Asp Ser Val Ile Gly Trp Val Leu Gly Thr Gly
225                 230                 235                 240

Thr Gln Leu Thr Val Leu
                245
```

<210> SEQ ID NO 39
<211> LENGTH: 246
<212> TYPE: PRT
<213> ORGANISM: Artificial Sequence
<220> FEATURE:
<223> OTHER INFORMATION: Laboratory synthesis

<400> SEQUENCE: 39

```
Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Lys Ser
            20                  25                  30

Ala Ile His Trp Val Arg Gln Ala Pro Gly Gln Gly Leu Glu Trp Met
        35                  40                  45

Gly Gly Val Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Trp Tyr Leu Asp Leu Trp Gly Arg Gly Thr Leu Val Thr
            100                 105                 110

Val Ser Ser Ala Ser Thr Gly Gly Ser Ser Arg Ser Ser Ser Ser Gly
        115                 120                 125

Gly Gly Gly Ser Gly Gly Gly Gly Leu Pro Val Leu Thr Gln Pro Pro
    130                 135                 140
```

```
Ser Ala Ser Gly Thr Pro Gly Gln Arg Val Thr Ile Ser Cys Ser Gly
145                 150                 155                 160

Ser Ser Ser Asn Ile Gly Gly Tyr Ser Val Asn Trp Tyr Gln Gln Phe
                165                 170                 175

Pro Gly Thr Ala Pro Lys Leu Leu Ile Tyr Arg Asn Asn Gln Arg Pro
            180                 185                 190

Ser Gly Val Pro Asp Arg Phe Ser Gly Ser Lys Ser Gly Ala Ser Ala
        195                 200                 205

Ser Leu Ala Ile Ser Gly Leu Gln Ser Glu Asp Val Ala Asp Tyr Tyr
    210                 215                 220

Cys Ala Ala Trp Asp Asp Ser Leu Ile Gly Tyr Val Phe Gly Thr Gly
225                 230                 235                 240

Thr Gln Leu Thr Val Leu
                245


<210> SEQ ID NO 40
<211> LENGTH: 246
<212> TYPE: PRT
<213> ORGANISM: Artificial Sequence
<220> FEATURE:
<223> OTHER INFORMATION: Laboratory synthesis

<400> SEQUENCE: 40

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Lys Ser
            20                  25                  30

Ala Ile Gln Trp Val Arg Gln Ala Pro Gly Gln Gly Leu Glu Trp Met
        35                  40                  45

Gly Gly Val Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Trp Tyr Leu Asp Leu Trp Gly Arg Gly Thr Leu Val Thr
            100                 105                 110

Val Ser Ser Ala Ser Thr Gly Gly Ser Ser Arg Ser Ser Ser Ser Gly
        115                 120                 125

Gly Gly Gly Ser Gly Gly Gly Gly Leu Pro Val Leu Thr Gln Pro Pro
    130                 135                 140

Ser Ala Ser Gly Thr Pro Gly Gln Arg Val Thr Ile Ser Cys Ser Gly
145                 150                 155                 160

Ser Ser Asn Asn Ile Gly Gly Tyr Ser Val Asn Trp Tyr Gln Gln Phe
                165                 170                 175

Pro Gly Thr Ala Pro Lys Leu Leu Ile Tyr Arg Asn Asn Gln Arg Pro
            180                 185                 190

Ser Gly Val Pro Asp Arg Phe Ser Gly Ser Lys Ser Gly Ala Ser Ala
        195                 200                 205

Ser Leu Ala Ile Ser Gly Leu Gln Ser Glu Asp Glu Ala Asp Tyr Tyr
    210                 215                 220

Cys Ala Ala Trp Asp Asp Ser Glu Ile Gly Trp Leu Phe Gly Thr Gly
225                 230                 235                 240

Thr Gln Leu Thr Val Leu
                245
```

<210> SEQ ID NO 41
<211> LENGTH: 696
<212> TYPE: PRT
<213> ORGANISM: Artificial Sequence
<220> FEATURE:
<223> OTHER INFORMATION: Laboratory synthesis

<400> SEQUENCE: 41

Gln Val Gln Leu Gln Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Gly Trp Tyr Phe Asp Leu Trp Gly Arg Gly Thr Leu Val Thr
100 105 110

Val Ser Ser Ala Ser Thr Lys Gly Pro Ser Val Phe Pro Leu Ala Pro
115 120 125

Cys Ser Arg Ser Thr Ser Glu Ser Thr Ala Ala Leu Gly Cys Leu Val
130 135 140

Lys Asp Tyr Phe Pro Glu Pro Val Thr Val Ser Trp Asn Ser Gly Ala
145 150 155 160

Leu Thr Ser Gly Val His Thr Phe Pro Ala Val Leu Gln Ser Ser Gly
165 170 175

Leu Tyr Ser Leu Ser Ser Val Val Thr Val Pro Ser Ser Ser Leu Gly
180 185 190

Thr Lys Thr Tyr Thr Cys Asn Val Asp His Lys Pro Ser Asn Thr Lys
195 200 205

Val Asp Lys Arg Val Glu Ser Lys Tyr Gly Pro Pro Cys Pro Pro Cys
210 215 220

Pro Ala Pro Glu Phe Leu Gly Gly Pro Ser Val Phe Leu Phe Pro Pro
225 230 235 240

Lys Pro Lys Asp Thr Leu Met Ile Ser Arg Thr Pro Glu Val Thr Cys
245 250 255

Val Val Val Asp Val Ser Gln Glu Asp Pro Glu Val Gln Phe Asn Trp
260 265 270

Tyr Val Asp Gly Val Glu Val His Asn Ala Lys Thr Lys Pro Arg Glu
275 280 285

Glu Gln Phe Asn Ser Thr Tyr Arg Val Val Ser Val Leu Thr Val Leu
290 295 300

His Gln Asp Trp Leu Asn Gly Lys Glu Tyr Lys Cys Lys Val Ser Asn
305 310 315 320

Lys Gly Leu Pro Ser Ser Ile Glu Lys Thr Ile Ser Lys Ala Lys Gly
325 330 335

Gln Pro Arg Glu Pro Gln Val Tyr Thr Leu Pro Pro Ser Gln Glu Glu
340 345 350

Met Thr Lys Asn Gln Val Ser Leu Thr Cys Leu Val Lys Gly Phe Tyr
355 360 365

Pro Ser Asp Ile Ala Val Glu Trp Glu Ser Asn Gly Gln Pro Glu Asn
370 375 380

Asn Tyr Lys Thr Thr Pro Pro Val Leu Asp Ser Asp Gly Ser Phe Phe
385 390 395 400

Leu Tyr Ser Arg Leu Thr Val Asp Lys Ser Arg Trp Gln Glu Gly Asn
405 410 415

Val Phe Ser Cys Ser Val Met His Glu Ala Leu His Asn His Tyr Thr
420 425 430

Gln Lys Ser Leu Ser Leu Ser Leu Gly Lys Gly Gly Gly Gly Ser Gly
435 440 445

Gly Gly Gly Ser Asp Ile Gln Met Thr Gln Ser Pro Ser Ser Leu Ser
450 455 460

Ala Ser Val Gly Asp Arg Val Thr Ile Thr Cys Arg Ala Ser Gln Asp
465 470 475 480

Ile Arg Asn Tyr Leu Asn Trp Tyr Gln Gln Lys Pro Gly Lys Ala Pro
485 490 495

Lys Leu Leu Ile Tyr Tyr Thr Ser Arg Leu Glu Ser Gly Val Pro Ser
500 505 510

Arg Phe Ser Gly Ser Gly Ser Gly Thr Asp Tyr Thr Leu Thr Ile Ser
515 520 525

Ser Leu Gln Pro Glu Asp Phe Ala Thr Tyr Tyr Cys Gln Gln Gly Asn
530 535 540

Thr Leu Pro Trp Thr Phe Gly Cys Gly Thr Lys Val Glu Ile Lys Gly
545 550 555 560

Gly Gly Gly Ser Gly Gly Gly Gly Ser Gly Gly Gly Gly Ser Glu Val
565 570 575

Gln Leu Val Glu Ser Gly Gly Gly Leu Val Gln Pro Gly Gly Ser Leu
580 585 590

Arg Leu Ser Cys Ala Ala Ser Gly Tyr Ser Phe Thr Gly Tyr Thr Met
595 600 605

Asn Trp Val Arg Gln Ala Pro Gly Lys Cys Leu Glu Trp Val Ala Leu
610 615 620

Ile Asn Pro Tyr Lys Gly Val Thr Thr Tyr Ala Asp Ser Val Lys Gly
625 630 635 640

Arg Phe Thr Ile Ser Val Asp Lys Ser Lys Asn Thr Ala Tyr Leu Gln
645 650 655

Met Asn Ser Leu Arg Ala Glu Asp Thr Ala Val Tyr Tyr Cys Ala Arg
660 665 670

Ser Gly Tyr Tyr Gly Asp Ser Asp Trp Tyr Phe Asp Val Trp Gly Gln
675 680 685

Gly Thr Leu Val Thr Val Ser Ser
690 695

<210> SEQ ID NO 42
<211> LENGTH: 216
<212> TYPE: PRT
<213> ORGANISM: Artificial Sequence
<220> FEATURE:
<223> OTHER INFORMATION: Laboratory synthesis

<400> SEQUENCE: 42

Leu Pro Val Leu Thr Gln Pro Pro Ser Ala Ser Gly Thr Pro Gly Gln
1 5 10 15

Arg Val Thr Ile Ser Cys Ser Gly Ser Ser Ser Asn Ile Gly Gly Tyr
20 25 30

```
Ser Val Asn Trp Tyr Gln Gln Phe Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Ala Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Ile Gly Tyr Val Phe Gly Thr Gly Thr Gln Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215


<210> SEQ ID NO 43
<211> LENGTH: 696
<212> TYPE: PRT
<213> ORGANISM: Artificial Sequence
<220> FEATURE:
<223> OTHER INFORMATION: Laboratory synthesis

<400> SEQUENCE: 43

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Lys Ser
            20                  25                  30

Ala Ile Met Trp Val Arg Gln Ala Pro Gly Gln Gly Leu Glu Trp Met
        35                  40                  45

Gly Gly Val Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Trp Tyr Leu Asp Leu Trp Gly Arg Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175
```

```
Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly Pro Pro Cys Pro Pro Cys
    210                 215                 220

Pro Ala Pro Glu Phe Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Lys Ser Leu Ser Leu Ser Leu Gly Lys Gly Gly Gly Gly Ser Gly
        435                 440                 445

Gly Gly Gly Ser Asp Ile Gln Met Thr Gln Ser Pro Ser Ser Leu Ser
    450                 455                 460

Ala Ser Val Gly Asp Arg Val Thr Ile Thr Cys Arg Ala Ser Gln Asp
465                 470                 475                 480

Ile Arg Asn Tyr Leu Asn Trp Tyr Gln Gln Lys Pro Gly Lys Ala Pro
                485                 490                 495

Lys Leu Leu Ile Tyr Tyr Thr Ser Arg Leu Glu Ser Gly Val Pro Ser
            500                 505                 510

Arg Phe Ser Gly Ser Gly Ser Gly Thr Asp Tyr Thr Leu Thr Ile Ser
        515                 520                 525

Ser Leu Gln Pro Glu Asp Phe Ala Thr Tyr Tyr Cys Gln Gln Gly Asn
    530                 535                 540

Thr Leu Pro Trp Thr Phe Gly Cys Gly Thr Lys Val Glu Ile Lys Gly
545                 550                 555                 560

Gly Gly Gly Ser Gly Gly Gly Gly Ser Gly Gly Gly Gly Ser Glu Val
                565                 570                 575

Gln Leu Val Glu Ser Gly Gly Gly Leu Val Gln Pro Gly Gly Ser Leu
            580                 585                 590

Arg Leu Ser Cys Ala Ala Ser Gly Tyr Ser Phe Thr Gly Tyr Thr Met
```

```
        595                 600                 605

Asn Trp Val Arg Gln Ala Pro Gly Lys Cys Leu Glu Trp Val Ala Leu
    610                 615                 620

Ile Asn Pro Tyr Lys Gly Val Thr Thr Tyr Ala Asp Ser Val Lys Gly
625                 630                 635                 640

Arg Phe Thr Ile Ser Val Asp Lys Ser Lys Asn Thr Ala Tyr Leu Gln
                645                 650                 655

Met Asn Ser Leu Arg Ala Glu Asp Thr Ala Val Tyr Tyr Cys Ala Arg
            660                 665                 670

Ser Gly Tyr Tyr Gly Asp Ser Asp Trp Tyr Phe Asp Val Trp Gly Gln
        675                 680                 685

Gly Thr Leu Val Thr Val Ser Ser
    690                 695
```

<210> SEQ ID NO 44
<211> LENGTH: 216
<212> TYPE: PRT
<213> ORGANISM: Artificial Sequence
<220> FEATURE:
<223> OTHER INFORMATION: Laboratory synthesis

<400> SEQUENCE: 44

```
Leu Pro Val Leu Thr Gln Pro Pro Ser Ala Ser Gly Thr Pro Gly Gln
1               5                   10                  15

Arg Val Thr Ile Ser Cys Ser Gly Ser Ser Asn Asn Ile Gly Gly Tyr
            20                  25                  30

Ser Val Asn Trp Tyr Gln Gln Phe Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Ala Ser Phe Ser Leu Ala Ile Ser Gly Leu Gln
65                  70                  75                  80

Phe Glu Asp Glu Ala Asp Tyr Tyr Cys Ala Arg Trp Asp Asp Ser Val
                85                  90                  95

Ile Gly Trp Val Leu Gly Thr Gly Thr Gln Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 45
<211> LENGTH: 696
<212> TYPE: PRT
<213> ORGANISM: Artificial Sequence
<220> FEATURE:
<223> OTHER INFORMATION: Laboratory synthesis

<400> SEQUENCE: 45

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Lys Ser
            20                  25                  30

Ala Ile His Trp Val Arg Gln Ala Pro Gly Gln Gly Leu Glu Trp Met
        35                  40                  45

Gly Gly Val Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Trp Tyr Leu Asp Leu Trp Gly Arg Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly Pro Pro Cys Pro Pro Cys
    210                 215                 220

Pro Ala Pro Glu Phe Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn

```
                405                 410                 415

Val Phe Ser Cys Ser Val Met His Glu Ala Leu His Asn His Tyr Thr
            420                 425                 430

Gln Lys Ser Leu Ser Leu Ser Leu Gly Lys Gly Gly Gly Gly Ser Gly
        435                 440                 445

Gly Gly Gly Ser Asp Ile Gln Met Thr Gln Ser Pro Ser Ser Leu Ser
    450                 455                 460

Ala Ser Val Gly Asp Arg Val Thr Ile Thr Cys Arg Ala Ser Gln Asp
465                 470                 475                 480

Ile Arg Asn Tyr Leu Asn Trp Tyr Gln Gln Lys Pro Gly Lys Ala Pro
                485                 490                 495

Lys Leu Leu Ile Tyr Tyr Thr Ser Arg Leu Glu Ser Gly Val Pro Ser
            500                 505                 510

Arg Phe Ser Gly Ser Gly Ser Gly Thr Asp Tyr Thr Leu Thr Ile Ser
        515                 520                 525

Ser Leu Gln Pro Glu Asp Phe Ala Thr Tyr Tyr Cys Gln Gln Gly Asn
    530                 535                 540

Thr Leu Pro Trp Thr Phe Gly Cys Gly Thr Lys Val Glu Ile Lys Gly
545                 550                 555                 560

Gly Gly Gly Ser Gly Gly Gly Gly Ser Gly Gly Gly Gly Ser Glu Val
                565                 570                 575

Gln Leu Val Glu Ser Gly Gly Gly Leu Val Gln Pro Gly Gly Ser Leu
            580                 585                 590

Arg Leu Ser Cys Ala Ala Ser Gly Tyr Ser Phe Thr Gly Tyr Thr Met
        595                 600                 605

Asn Trp Val Arg Gln Ala Pro Gly Lys Cys Leu Glu Trp Val Ala Leu
    610                 615                 620

Ile Asn Pro Tyr Lys Gly Val Thr Thr Tyr Ala Asp Ser Val Lys Gly
625                 630                 635                 640

Arg Phe Thr Ile Ser Val Asp Lys Ser Lys Asn Thr Ala Tyr Leu Gln
                645                 650                 655

Met Asn Ser Leu Arg Ala Glu Asp Thr Ala Val Tyr Tyr Cys Ala Arg
            660                 665                 670

Ser Gly Tyr Tyr Gly Asp Ser Asp Trp Tyr Phe Asp Val Trp Gly Gln
        675                 680                 685

Gly Thr Leu Val Thr Val Ser Ser
    690                 695


<210> SEQ ID NO 46
<211> LENGTH: 216
<212> TYPE: PRT
<213> ORGANISM: Artificial Sequence
<220> FEATURE:
<223> OTHER INFORMATION: Laboratory synthesis

<400> SEQUENCE: 46

Leu Pro Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Gly Tyr
            20                  25                  30

Ser Val Asn Trp Tyr Gln Gln Phe Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Ala Ser Ala Ser Leu Ala Ile Ser Gly Leu Gln
```

-continued

```
65                  70                  75                  80

Ser Glu Asp Val Ala Asp Tyr Tyr Cys Ala Ala Trp Asp Asp Ser Leu
                85                  90                  95

Ile Gly Tyr Val Phe Gly Thr Gly Thr Gln Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215


<210> SEQ ID NO 47
<211> LENGTH: 696
<212> TYPE: PRT
<213> ORGANISM: Artificial Sequence
<220> FEATURE:
<223> OTHER INFORMATION: Laboratory synthesis

<400> SEQUENCE: 47

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Lys Ser
            20                  25                  30

Ala Ile Gln Trp Val Arg Gln Ala Pro Gly Gln Gly Leu Glu Trp Met
        35                  40                  45

Gly Gly Val Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Trp Tyr Leu Asp Leu Trp Gly Arg Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly Pro Pro Cys Pro Pro Cys
```

```
    210                 215                 220

Pro Ala Pro Glu Phe Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Lys Ser Leu Ser Leu Ser Leu Gly Lys Gly Gly Gly Gly Ser Gly
        435                 440                 445

Gly Gly Gly Ser Asp Ile Gln Met Thr Gln Ser Pro Ser Ser Leu Ser
    450                 455                 460

Ala Ser Val Gly Asp Arg Val Thr Ile Thr Cys Arg Ala Ser Gln Asp
465                 470                 475                 480

Ile Arg Asn Tyr Leu Asn Trp Tyr Gln Gln Lys Pro Gly Lys Ala Pro
                485                 490                 495

Lys Leu Leu Ile Tyr Tyr Thr Ser Arg Leu Glu Ser Gly Val Pro Ser
            500                 505                 510

Arg Phe Ser Gly Ser Gly Ser Gly Thr Asp Tyr Thr Leu Thr Ile Ser
        515                 520                 525

Ser Leu Gln Pro Glu Asp Phe Ala Thr Tyr Tyr Cys Gln Gln Gly Asn
    530                 535                 540

Thr Leu Pro Trp Thr Phe Gly Cys Gly Thr Lys Val Glu Ile Lys Gly
545                 550                 555                 560

Gly Gly Gly Ser Gly Gly Gly Gly Ser Gly Gly Gly Gly Ser Glu Val
                565                 570                 575

Gln Leu Val Glu Ser Gly Gly Gly Leu Val Gln Pro Gly Gly Ser Leu
            580                 585                 590

Arg Leu Ser Cys Ala Ala Ser Gly Tyr Ser Phe Thr Gly Tyr Thr Met
        595                 600                 605

Asn Trp Val Arg Gln Ala Pro Gly Lys Cys Leu Glu Trp Val Ala Leu
    610                 615                 620

Ile Asn Pro Tyr Lys Gly Val Thr Thr Tyr Ala Asp Ser Val Lys Gly
625                 630                 635                 640
```

Arg Phe Thr Ile Ser Val Asp Lys Ser Lys Asn Thr Ala Tyr Leu Gln
645 650 655

Met Asn Ser Leu Arg Ala Glu Asp Thr Ala Val Tyr Tyr Cys Ala Arg
660 665 670

Ser Gly Tyr Tyr Gly Asp Ser Asp Trp Tyr Phe Asp Val Trp Gly Gln
675 680 685

Gly Thr Leu Val Thr Val Ser Ser
690 695

<210> SEQ ID NO 48
<211> LENGTH: 216
<212> TYPE: PRT
<213> ORGANISM: Artificial Sequence
<220> FEATURE:
<223> OTHER INFORMATION: Laboratory synthesis

<400> SEQUENCE: 48

Leu Pro Val Leu Thr Gln Pro Pro Ser Ala Ser Gly Thr Pro Gly Gln
1 5 10 15

Arg Val Thr Ile Ser Cys Ser Gly Ser Ser Asn Asn Ile Gly Gly Tyr
20 25 30

Ser Val Asn Trp Tyr Gln Gln Phe Pro Gly Thr Ala Pro Lys Leu Leu
35 40 45

Ile Tyr Arg Asn Asn Gln Arg Pro Ser Gly Val Pro Asp Arg Phe Ser
50 55 60

Gly Ser Lys Ser Gly Ala Ser Ala Ser Leu Ala Ile Ser Gly Leu Gln
65 70 75 80

Ser Glu Asp Glu Ala Asp Tyr Tyr Cys Ala Ala Trp Asp Asp Ser Glu
85 90 95

Ile Gly Trp Leu Phe Gly Thr Gly Thr Gln Leu Thr Val Leu Gly Gln
100 105 110

Pro Lys Ala Ala Pro Ser Val Thr Leu Phe Pro Pro Ser Ser Glu Glu
115 120 125

Leu Gln Ala Asn Lys Ala Thr Leu Val Cys Leu Ile Ser Asp Phe Tyr
130 135 140

Pro Gly Ala Val Thr Val Ala Trp Lys Ala Asp Ser Ser Pro Val Lys
145 150 155 160

Ala Gly Val Glu Thr Thr Thr Pro Ser Lys Gln Ser Asn Asn Lys Tyr
165 170 175

Ala Ala Ser Ser Tyr Leu Ser Leu Thr Pro Glu Gln Trp Lys Ser His
180 185 190

Arg Ser Tyr Ser Cys Gln Val Thr His Glu Gly Ser Thr Val Glu Lys
195 200 205

Thr Val Ala Pro Thr Glu Cys Ser
210 215

<210> SEQ ID NO 49
<211> LENGTH: 442
<212> TYPE: PRT
<213> ORGANISM: Artificial Sequence
<220> FEATURE:
<223> OTHER INFORMATION: Laboratory synthesis

<400> SEQUENCE: 49

Gln Val Gln Leu Gln Gln Ser Gly Ala Glu Val Lys Lys Pro Gly Ser
1 5 10 15

Ser Val Lys Val Ser Cys Lys Ala Ser Gly Gly Thr Phe Ser Ser Tyr

-continued

```
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Trp Tyr Phe Asp Leu Trp Gly Arg Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly Pro Pro Cys Pro Pro Cys
    210                 215                 220

Pro Ala Pro Glu Phe Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Lys Ser Leu Ser Leu Ser Leu Gly Lys
        435                 440
```

<210> SEQ ID NO 50
<211> LENGTH: 442
<212> TYPE: PRT
<213> ORGANISM: Artificial Sequence
<220> FEATURE:
<223> OTHER INFORMATION: Laboratory synthesis

<400> SEQUENCE: 50

```
Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Lys Ser
            20                  25                  30

Ala Ile Met Trp Val Arg Gln Ala Pro Gly Gln Gly Leu Glu Trp Met
        35                  40                  45

Gly Gly Val Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Trp Tyr Leu Asp Leu Trp Gly Arg Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly Pro Pro Cys Pro Pro Cys
    210                 215                 220

Pro Ala Pro Glu Phe Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
        355                 360                 365
```

```
Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Lys Ser Leu Ser Leu Ser Leu Gly Lys
        435                 440


<210> SEQ ID NO 51
<211> LENGTH: 442
<212> TYPE: PRT
<213> ORGANISM: Artificial Sequence
<220> FEATURE:
<223> OTHER INFORMATION: Laboratory synthesis

<400> SEQUENCE: 51

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Lys Ser
            20                  25                  30

Ala Ile His Trp Val Arg Gln Ala Pro Gly Gln Gly Leu Glu Trp Met
        35                  40                  45

Gly Gly Val Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Trp Tyr Leu Asp Leu Trp Gly Arg Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly Pro Pro Cys Pro Pro Cys
    210                 215                 220

Pro Ala Pro Glu Phe Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285
```

```
Glu Gln Phe Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Lys Ser Leu Ser Leu Ser Leu Gly Lys
        435                 440


<210> SEQ ID NO 52
<211> LENGTH: 442
<212> TYPE: PRT
<213> ORGANISM: Artificial Sequence
<220> FEATURE:
<223> OTHER INFORMATION: Laboratory synthesis

<400> SEQUENCE: 52

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Lys Ser
            20                  25                  30

Ala Ile Gln Trp Val Arg Gln Ala Pro Gly Gln Gly Leu Glu Trp Met
        35                  40                  45

Gly Gly Val Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Trp Tyr Leu Asp Leu Trp Gly Arg Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205
```

-continued

```
Val Asp Lys Arg Val Glu Ser Lys Tyr Gly Pro Pro Cys Pro Pro Cys
    210                 215                 220

Pro Ala Pro Glu Phe Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Lys Ser Leu Ser Leu Ser Leu Gly Lys
        435                 440
```